(12) United States Patent
Anderson et al.

(10) Patent No.: US 7,538,088 B2
(45) Date of Patent: May 26, 2009

(54) METHOD FOR INHIBITING ANGIOGENESIS BY ADMINISTRATION OF THE EXTRACELLULAR DOMAIN OF D1-1 POLYPEPTIDE

(75) Inventors: David J. Anderson, Altadena, CA (US); Hai U. Wang, Eldorado Hills, CA (US); Donghun Shin, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 457 days.

(21) Appl. No.: 10/424,986

(22) Filed: Apr. 28, 2003

(65) Prior Publication Data

US 2004/0120955 A1 Jun. 24, 2004

Related U.S. Application Data

(60) Provisional application No. 60/375,904, filed on Apr. 26, 2002.

(51) Int. Cl.
*A61K 38/17* (2006.01)
*C07K 14/47* (2006.01)
*C07K 14/515* (2006.01)

(52) U.S. Cl. .......................... 514/12; 530/300; 530/324
(58) Field of Classification Search ........................ None
See application file for complete search history.

(56) References Cited

U.S. PATENT DOCUMENTS

2004/0120955 A1  6/2004  Anderson et al.

FOREIGN PATENT DOCUMENTS

| EP | 0 682 113 A2 | 11/1995 |
|---|---|---|
| WO | WO-00/55173 A1 | 9/2000 |
| WO | WO-00/61623 A1 | 10/2000 |
| WO | WO-01/57190 A2 | 8/2001 |
| WO | WO-01/77289 A2 | 10/2001 |
| WO | WO-02/079492 A2 | 10/2002 |

OTHER PUBLICATIONS

Staton et al, 2004. Int J Exp Path. 85: 233-248).*
Wells (Sep. 18, 1990) Biochemistry 29(37): 8509-5817.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Armstrong et al. 2008. Arterioscler Thromb Vasc Biol. 28:1-7.*
Ferrer-Costa (2007. J Mol Biol. 365: 249-256).*
Auerbach, 2003. Clinical Chemistry. 49(1): 32-40.*

(Continued)

*Primary Examiner*—Elizabeth C. Kemmerer
*Assistant Examiner*—Zachary C Howard
(74) *Attorney, Agent, or Firm*—Ropes & Gray LLP

(57) ABSTRACT

The disclosure provides, among other things, novel angiogenesis-related nucleic acids, polypeptides and methods of use.

6 Claims, 15 Drawing Sheets

Human D1-1 Polypeptides

A. Full-length sequence (SEQ ID NO:10)

```
MGTAGAMQLCWVILGFLLFRGHNSQPTMTQTSSSQGGLGGLSLTTEPVSS 50
NPGYIPSSEANRPSHLSSTGTPGAGVPSSGRDGGTSRDTFQTVPPNSTTM 100
SLSMREDATILPSPTSETVLTVAAFGVISFIVILVVVVIILVGVVSLRFK 150
CRKSKESEDPQKPGSSGLSESCSTANGEKDSITLISMKNINMNNGKQSLS 200
AEKVL 205
```

B. Extracellular portion (SEQ ID NO:11)

```
QPTMTQTSSSQGGLGGLSLTTEPVSSNPGYIPSSEANRPSHLSSTGTPGA
GVPSSGRDGGTSRDTFQTVPPNSTTMSLSMREDATILPSPTSETVLT
```

C. Conserved portion (SEQ ID NO:12)

```
VAAFGVISFIVILVVVVIILVGVVSLRFKCRKSKESEDPQKPGSSGLSES
CSTANGEKDSITLISMKNINMNNGKQSLSAEKVL
```

OTHER PUBLICATIONS

Antikaninen et al, 2005, Bioorganic & Medicinal Chemistry. 13: 2701-2716.*

Ponce et al, 2003. Current Protocols in Cell Biology. Supplement 18, pp. 19.5.1-19.5.6 (6 pages total).*

Marra, M., et al., Accession No. AA267694 (Mar. 21, 1997).

Genbank ref. No. XM_148854.

Genbank ref No. XP_148854.

Delisser et al., "Platelet endothelial cell adhesion molecule (CD31)," Current Topics in Microbiology and Immunology, 184: 37-45 (1993).

Osborn et al., "Direct expression cloning of vascular cell adhesion molecule1, a cytokine-induced endothelial protein that binds to lymphocytes,"Cell, 59: 1203-1211 (1989).

* cited by examiner

Figure 1

Figure 5: Murine D1-1 Nucleic Acids

A. cDNA sequence (SEQ ID NO:1)

GAGCCTGCTACACACCCAGCTGATCTGGGGACCAGCGGAGCCATGAGGCTGGGTT
CAGCAATTCTCGGTTTACTCCTGCTCCAAGGCTACAGCTCT CAACCTACGACAAC
TCAGACCTCGCAGGAAATTCTACAGAAGTCTTCTCAGGTCTCCTTGGTATCCAAT
CAGCCTGTGACACCAAGGTCAAGCACCATGGATAAACAGTCCCTTTCCTTGCCTG
ACTTGATGTCCTTCCAGCCACAGAAGCACACACTGGGACCTGGCACAGGAACCCC
AGAAAGGAGCAGCAGCAGCAGCAGCAGCAGCAGCAGCAGGAGAGGAGAAGCATCT
CTGGATGCTACTCCCAGTCCAGAAACCACCAGCCTTCAGACAAAAAAGATGACCA
TCCTGCTGACCATCCTGCCTACCCCACATCAGAGTCAGTGCTAACT GTGGCTGC
CTTTGGTGTCATCAGCTTCATTGTCATCCTGGTGGTTGTAGTGATCATCCTGGTC
AGTGTGGTCAGTCTAAGATTTAAGTGTCGGAAGAACAAGGAGTCTGAAGATCCAC
AGAAACCAGGGAGTTCAGGACTGTCTGAAAGCTGCTCAACAGCCAATGGAGAGAA
AGACAGCATCACACTCATCTCCATGAGGAACATCAACGTGAACAACAGCAAAGGC
AGCATGTCAGCAGAGAAGATTCTT TAAGAGTGACCTGGAGTCGCCATGGGTCCAC
GTGTGCGGCTGTCCCCTGGCCATGAGGAAGGAGAGGAGACGAGATTGGGGGAGGC
AGCGGACCACACATAAATTATTTGATGTCATGCCTGCTCCCAGTTCTAAAGGACA
TGAGATTCCTCTAGATCCAGAAGAACCTACCACACAAGAGACTCCTTCCCACTTG
GAAGCCATGCTAGACACTTGGCCTGCTCCCCCTCCTCCTGCTGCTCAGAAACTCA
GGAACGAGGAGTCAATAGAGCAAGACTTAAGGAAATAATGAGGTAGATTGTCCAT
TCTACTAGAATTAAAATTATTTTCTGGCCTGG

B. Sequence encoding extracellular portion (SEQ ID NO:2)

CAACCTACGACAACTCAGACCTCGCAGGAAATTCTACAGAAGTCTTCTCAGGTCT
CCTTGGTATCCAATCAGCCTGTGACACCAAGGTCAAGCACCATGGATAAACAGTC
CCTTTCCTTGCCTGACTTGATGTCCTTCCAGCCACAGAAGCACACACTGGGACCT
GGCACAGGAACCCCAGAAAGGAGCAGCAGCAGCAGCAGCAGCAGCAGCAGCAGGA
GAGGAGAAGCATCTCTGGATGCTACTCCCAGTCCAGAAACCACCAGCCTTCAGAC
AAAAAAGATGACCATCCTGCTGACCATCCTGCCTACCCCACATCAGAGTCAGTG
CTAACT

C. Sequence encoding conserved portion (SEQ ID NO:3)

GTGGCTGCCTTTGGTGTCATCAGCTTCATTGTCATCCTGGTGGTTGTAGTGATCA
TCCTGGTCAGTGTGGTCAGTCTAAGATTTAAGTGTCGGAAGAACAAGGAGTCTGA
AGATCCACAGAAACCAGGGAGTTCAGGACTGTCTGAAAGCTGCTCAACAGCCAAT
GGAGAGAAAGACAGCATCACACTCATCTCCATGAGGAACATCAACGTGAACAACA
GCAAAGGCAGCATGTCAGCAGAGAAGATTCTT

Figure 6: Murine D1-1 Polypeptides

A. Full-length sequence (SEQ ID NO:4)

MRLGSAILGLLLLQGYSSQPTTTQTSQEILQKSSQVSLVSNQPVTPRSST 50
MDKQSLSLPDLMSFQPQKHTLGPGTGTPERSSSSSSSSSSSRRGEASLDAT 100
PSPETTSLQTKKMTILLTILPTPTSESVLTVAAFGVISFIVILVVVVIIL 150
VSVVSLRFKCRKNKESEDPQKPGSSGLSESCSTANGEKDSITLISMRNIN 200
VNNSKGSMSAEKIL 214

B. Extracellular portion (SEQ ID NO:5)

SQPTTTQTSQEILQKSSQVSLVSNQPVTPRSSTMDKQSLSLPDLMSFQPQK
HTLGPGTGTPERSSSSSSSSSSSRRGEASLDATPSPETTSLQTKKMTILLTI
LPTPTSESVLT

C. Conserved portion (SEQ ID NO:6)

VAAFGVISFIVILVVVVIILVSVVSLRFKCRKNKESEDPQKPGSSGLSESC
STANGEKDSITLISMRNINVNNSKGSMSAEKIL

Figure 7: Human D1-1 Nucleic Acids

A. cDNA sequence (SEQ ID NO: 7)

GAGCCTCCACTGAGCTGCTGCCTGCCCGCCACATACCCAGCTGAC<u>ATGGGCAC</u>
<u>CGCAGGAGCCATGCAGCTGTGCTGGGTGATCCTGGGCTTCCTCCTGTTCCGAG</u>
<u>GCCACAACTCCCAGCCCACAATGACCCAGACCTCTAGCTCTCAGGGAGGCCTT</u>
<u>GGCGGTCTAAGTCTGACCACAGAGCCAGTTTCTTCCAACCCAGGATACATCCC</u>
<u>TTCCTCAGAGGCTAACAGGCCAAGCCATCTGTCCAGCACTGGTACCCCAGGCG</u>
<u>CAGGTGTCCCCAGCAGTGGAAGAGACGGAGGCACAAGCAGAGACACATTTCAA</u>
<u>ACTGTTCCCCCAATTCAACCACCATGAGCCTGAGCATGAGGGAAGATGCGAC</u>
<u>CATCCTGCCCAGCCCCACGTCAGAGACTGTGCTCACTGTGGCTGCATTTGGTG</u>
<u>TTATCAGCTTCATTGTCATCCTGGTGGTTGTGGTGATCATCCTAGTTGGTGTG</u>
<u>GTCAGCCTGAGGTTCAAGTGTCGGAAGAGCAAGGAGTCTGAAGATCCCCAGAA</u>
<u>ACCTGGGAGTTCAGGGCTGTCTGAAAGCTGCTCCACAGCCAATGGAGAGAAAG</u>
<u>ACAGCATCACCCTTATCTCCATGAAGAACATCAACATGAATAATGGCAAACAA</u>
<u>AGTCTCTCAGCAGAGAAGGTTCTTTANAAGCAACTTTGGGTCCCCATGAGTCC</u>
AAGGATGATGCAGCTGCCCTGTGACTACAAGGAGGAAGAGATGGAATTAGTAG
AGGCAATGAACCACATGTAAATTATTTTATTGTTTCATGTCTGCTTCTAGATC
TANAGGACACTAGCATTGCCCCAGATCTGGGGAGCAGCTACCAACAGGGGGAG
ACTCTTTTCCTGTATGGACAGCTGCTGTGGAAAATACTGGCCTGGCTTCTCCC
CACTCCTCAGAGC

B. Sequence encoding the extracellular portion (SEQ ID NO:8)

CAGCCCACAATGACCCAGACCTCTAGCTCTCAGGGAGGCCTTGGCGGTCTAAG
TCTGACCACAGAGCCAGTTTCTTCCAACCCAGGATACATCCCTTCCTCAGAGG
CTAACAGGCCAAGCCATCTGTCCAGCACTGGTACCCCAGGCGCAGGTGTCCCC
AGCAGTGGAAGAGACGGAGGCACAAGCAGAGACACATTTCAAACTGTTCCCCC
CAATTCAACCACCATGAGCCTGAGCATGAGGGAAGATGCGACCATCCTGCCCA
GCCCCACGTCAGAGACTGTGCTCACT

C. Sequence encoding the conserved portion (SEQ ID NO:9)

GTGGCTGCATTTGGTGTTATCAGCTTCATTGTCATCCTGGTGGTTGTGGTGAT
CATCCTAGTTGGTGTGGTCAGCCTGAGGTTCAAGTGTCGGAAGAGCAAGGAGT
CTGAAGATCCCCAGAAACCTGGGAGTTCAGGGCTGTCTGAAAGCTGCTCCACA
GCCAATGGAGAGAAAGACAGCATCACCCTTATCTCCATGAAGAACATCAACAT
GAATAATGGCAAACAAAGTCTCTCAGCAGAGAAGGTTCTTTANAAGCAACTTT
GGGTCCCCATGAGTCCAAGGATGATGCAGCTGCCCTGTGACTACAAGGAGGAA
GAGATGGAATTAGTAGAGGCAATGAACCACATGTAAATTATTTTATTGTTTCA
TGTCTGCTTC

Figure 8: Human D1-1 Polypeptides

A. Full-length sequence (SEQ ID NO:10)

MGTAGAMQLCWVILGFLLFRGHNSQPTMTQTSSSQGGLGGLSLTTEPVSS 50
NPGYIPSSEANRPSHLSSTGTPGAGVPSSGRDGGTSRDTFQTVPPNSTTM 100
SLSMREDATILPSPTSETVLTVAAFGVISFIVILVVVVIILVGVVSLRFK 150
CRKSKESEDPQKPGSSGLSESCSTANGEKDSITLISMKNINMNNGKQSLS 200
AEKVL 205

B. Extracellular portion (SEQ ID NO:11)

QPTMTQTSSSQGGLGGLSLTTEPVSSNPGYIPSSEANRPSHLSSTGTPGA
GVPSSGRDGGTSRDTFQTVPPNSTTMSLSMREDATILPSPTSETVLT

C. Conserved portion (SEQ ID NO:12)

VAAFGVISFIVILVVVVIILVGVVSLRFKCRKSKESEDPQKPGSSGLSES
CSTANGEKDSITLISMKNINMNNGKQSLSAEKVL

Figure 9: Bovine D1-1 Nucleic Acids

A. cDNA sequence (SEQ ID NO:13)

ACAGAGGCTGCCTGCCGGTTGCAGACCAAGCTGACATGGGGAGTGTCAGAGAAA
CGCAGCTGCGCTGGGCCATCCTGGGCTTCCTCCTGCTCCAAGGAGCCTTCAGCA
GTCAAAGTTCAACCACACAGCCAGCTTCCCCTGAAACAAGTCCTTCCACAGAGG
CCAACAGCTTAAGCCCTCTGTCCGGCACCTGGACCACAGCAGCATCAGAGACGC
CCTCACAGTTCTCCACGGAAGCCATGACTCTGAGTTCAAGCACCGTGGCTGATC
ACTTGCCGTCCTCTCCGGGACCGACTTGGTCCCAGTCACAGAAACACACGTCAG
GACTCAGCGCTGATGTTCCGAGCAGTGGCAGGAGCAGCGACAGCATGAGTGGAG
ACACCTCTCACAATGTTACTTCCACATCACCCAACATGAGTTTTAGGACGACAG
CAGACTCCACTGTCCCACCCAGCCCCACGTCAGAGACGGTGCTCACTGTGGCTG
CATTTGGTGTTATCAGCTTCATTGCCATCCTAGTGGTTGTGGTGATTGTCCTGG
TCAGTGTGGTCAGTCTAAGGTTTAAGTGTCGGAAGAACAAGGAGTCTGAAGATC
CCCAGAAACCTGGGAGTTCAGGGCTCTCTGAAAGCGGTTCCACAGCCAATGGAG
AGAAAGAGAGCATCACTCTTATCTCGATGAAGAACATCAACATGAATAACAGCA
AAGGATGCCCCTCA

B. Sequence encoding extracellular portion (SEQ ID NO:14)

CAAAGTTCAACCACACAGCCAGCTTCCCCTGAAACAAGTCCTTCCACAGAGGCC
AACAGCTTAAGCCCTCTGTCCGGCACCTGGACCACAGCAGCATCAGAGACGCCC
TCACAGTTCTCCACGGAAGCCATGACTCTGAGTTCAAGCACCGTGGCTGATCAC
TTGCCGTCCTCTCCGGGACCGACTTGGTCCCAGTCACAGAAACACACGTCAGGA
CTCAGCGCTGATGTTCCGAGCAGTGGCAGGAGCAGCGACAGCATGAGTGGAGAC
ACCTCTCACAATGTTACTTCCACATCACCCAACATGAGTTTTAGGACGACAGCA
GACTCCACTGTCCCACCCAGCCCCACGTCAGAGACGGTGCTCACT

C. Sequence encoding conserved portion (SEQ ID NO:15)

GTGGCTGCATTTGGTGTTATCAGCTTCATTGCCATCCTAGTGGTTGTGGTGATT
GTCCTGGTCAGTGTGGTCAGTCTAAGGTTTAAGTGTCGGAAGAACAAGGAGTCT
GAAGATCCCCAGAAACCTGGGAGTTCAGGGCTCTCTGAAAGCGGTTCCACAGCC
AATGGAGAGAAAGAGAGCATCACTCTTATCTCGATGAAGAACATCAACATGAAT
AACAGCAAAGGATGCCCCTCA

Figure 10: Bovine D1-1 Polypeptides

A. Full-length sequence (SEQ ID NO:16)

RGCLPVADQADMGSVRE<u>TQLRWAILGFLLLQGAFS</u>SQSSTTQPASPETSP
STEANSLSPLSGTWTTAASETPSQFSTEAMTLSSSTVADHLPSSPGPTWS
QSQKHTSGLSADVPSSGRSSDSMSGDTSHNVTSTSPNMSFRTTADSTVPP
SPTSETVLTVAAFGVISFIAILVVVVTIVLVSVVSLRFKCRKNKESEDPQ
KPGSSGLSESGSTANGEKESITLISMKNIINMNNSKGCPS

B. Extracellular portion (SEQ ID NO:17)

SQSSTTQPASPETSPSTEANSLSPLSGTWTTAASETPSQFSTEAMTLSSS
TVADHLPSSPGPTWSQSQKHTSGLSADVPSSGRSSDSMSGDTSHNVTSTS
PNMSFRTTADSTVPPSPTSETVLT

C. Conserved portion (SEQ ID NO:18)

VAAFGVISFIAILVVVVTIVLVSVVSLRFKCRKNKESEDPQKPGSSGLSES
GSTANGEKESITLISMKNIINMNNSKGCPS

Figure 11: Porcine D1-1 Nucleic Acids

A. cDNA sequence (SEQ ID NO:19)

CCCACGCGTCCGCGCCAGCCTGCCCCGTCCCACTGACATGGGGAGCGTCGGAGAAACGCA
GCTGTGCTGGGCCATCCTGGGCTTCCTCCTGCTCCAAGGCCACGGCTCCCAGCTCACAAT
ACCTAGCCCTCAGGGAGAGAGTCCTTCCGCAGAGTCCAACAGCTCAAGCCCTCTATCCAG
CAGCACCAGCAGCAGCAGCAACAGCAGCAGCAGCACCAGCACCACAGACACCCCTCACAA
TGGTACGTCCACGTCACCCACCGTGAGTCTGAGAACCAGAGAAGACCCGACCGTCCTGCC
CAGCCCCACGTCAGAGACGGTGCTCACAGTGGCCGCCTTTGGTGTCATCAGCTTCATTGT
CATCCTGCTGGTTGTGGTGATCATCCTGGTCAGCGTGGTCAGTCTAAGGTTTAAGTGTCG
GAGGAACAAGGAATCTGAAGATCCCCAGAAACCTGGGAGTTCGGGGCTCTCTGAAAGCTG
CTCCACAGCCAATGGAGAGAAAGACAGCATCACCCTCATCTCCATGAAAAATATCAACAT
GAATAACAGC

B. Sequence encoding extracellular portion (SEQ ID NO:20)

CAGCTCACAATACCTAGCCCTCAGGGAGAGAGTCCTTCCGCAGAGTCCAACAGCTCAAGC
CCTCTATCCAGCAGCACCAGCAGCAGCAGCAACAGCAGCAGCAGCACCAGCACCACAGAC
ACCCCTCACAATGGTACGTCCACGTCACCCACCGTGAGTCTGAGAACCAGAGAAGACCCG
ACCGTCCTGCCCAGCCCCACGTCAGAGACGGTGCTCACA

C. Sequence encoding conserved portion (SEQ ID NO:21)

GTGGCCGCCTTTGGTGTCATCAGCTTCATTGTCATCCTGCTGGTTGTGGTGATCATCCTG
GTCAGCGTGGTCAGTCTAAGGTTTAAGTGTCGGAGGAACAAGGAATCTGAAGATCCCCAG
AAACCTGGGAGTTCGGGGCTCTCTGAAAGCTGCTCCACAGCCAATGGAGAGAAAGACAGC
ATCACCCTCATCTCCATGAAAAATATCAACATGAATAACAGC

Figure 12: Porcine D1-1 Polypeptide Sequences

A. Sequence (SEQ ID NO:22)

PRVRASLPRPTDMGSVGETQLCWAILGFLLLQGHGSQLTIPSPQGESPSA
ESNSSSPLSSSTSSSSNSSSSTSTTDTPHNGTSTSPTVSLRTREDPTVLP
SPTSETVLTVAAFGVISFIVILLVVVIILVSVVSLRFKCRRNKESEDPQK
PGSSGLSESCSTANGEKDSITLISMKNINMNNS

B. Extracellular portion (SEQ ID NO:23)

QLTIPSPQGESPSAESNSSSPLSSSTSSSSNSSSSTSTTDTPHNGTSTSPT
VSLRTREDPTVLPSPTSETVLT

C. Conserved portion (SEQ ID NO:24)

VAAFGVISFIVILLVVVIILVSVVSLRFKCRRNKESEDPQKPGSSGLSESC
STANGEKDSITLISMKNINMNNS

SEQUENCE LISTING

<160> NUMBER OF SEQ ID NOS: 28

<210> SEQ ID NO 1
<211> LENGTH: 1022
<212> TYPE: DNA
<213> ORGANISM: Mus musculus

<400> SEQUENCE: 1
gagcctgcta cacacccagc tgatctgggg accagcggag ccatgaggct gggttcagca    60

-continued

```
attctcggtt tactcctgct ccaaggctac agctctcaac ctacgacaac tcagacctcg    120
caggaaattc tacagaagtc ttctcaggtc tccttggtat ccaatcagcc tgtgacacca    180
aggtcaagca ccatggataa acagtccctt tccttgcctg acttgatgtc cttccagcca    240
cagaagcaca cactgggacc tggcacagga accccagaaa ggagcagcag cagcagcagc    300
agcagcagca gcaggagagg agaagcatct ctggatgcta ctcccagtcc agaaaccacc    360
agccttcaga caaaaaagat gaccatcctg ctgaccatcc tgcctacccc cacatcagag    420
tcagtgctaa ctgtggctgc ctttggtgtc atcagcttca ttgtcatcct ggtggttgta    480
gtgatcatcc tggtcagtgt ggtcagtcta agatttaagt gtcggaagaa caaggagtct    540
gaagatccac agaaaccagg gagttcagga ctgtctgaaa gctgctcaac agccaatgga    600
gagaaagaca gcatcacact catctccatg aggaacatca cgtgaacaa cagcaaaggc     660 agcatgtcag cagagaagat tctttaagag tgacctggag tcgccatggg tccacgtgtg    720
cggctgtccc ctggccatga ggaaggagag gagacgagat tggggaggc agcggaccac     780 acataaatta tttgatgtca tgcctgctcc cagttctaaa ggacatgaga ttcctctaga    840
tccagaagaa cctaccacac aagagactcc ttcccacttg gaagccatgc tagacacttg    900
gcctgctccc cctcctcctg ctgctcagaa actcaggaac gaggagtcaa tagagcaaga    960
cttaaggaaa taatgaggta gattgtccat tctactagaa ttaaaattat tttctggcct   1020
gg                                                                  1022

<210> SEQ ID NO 2
<211> LENGTH: 336
<212> TYPE: DNA
<213> ORGANISM: Mus musculus

<400> SEQUENCE: 2
caacctacga caactcagac ctcgcaggaa attctacaga agtcttctca ggtctccttg     60
gtatccaatc agcctgtgac accaaggtca agcaccatgg ataaacagtc cctttccttg    120
cctgacttga tgtccttcca gccacagaag cacacactgg gacctggcac aggaaccccca   180 gaaaggagca gcagcagcag cagcagcagc agcaggagga ggagaagc atctctggat      240 gctactccca gtccagaaac caccagcctt cagacaaaaa agatgaccat cctgctgacc    300
atcctgccta cccccacatc agagtcagtg ctaact                              336

<210> SEQ ID NO 3
<211> LENGTH: 252
<212> TYPE: DNA
<213> ORGANISM: Mus musculus

<400> SEQUENCE: 3
gtggctgcct ttggtgtcat cagcttcatt gtcatcctgg tggttgtagt gatcatcctg     60
gtcagtgtgg tcagtctaag atttaagtgt cggaagaaca aggagtctga agatccacag    120
aaaccaggga gttcaggact gtctgaaagc tgctcaacag ccaatggaga gaaagacagc    180
atcacactca tctccatgag gaacatcaac gtgaacaaca gcaaaggcag catgtcagca    240
gagaagattc tt                                                        252

<210> SEQ ID NO 4
<211> LENGTH: 214
<212> TYPE: PRT
<213> ORGANISM: Mus musculus

<400> SEQUENCE: 4
```

Met Arg Leu Gly Ser Ala Ile Leu Gly Leu Leu Leu Gln Gly Tyr
1               5                   10                  15

Ser Ser Gln Pro Thr Thr Thr Gln Thr Ser Gln Glu Ile Leu Gln Lys
            20                  25                  30

Ser Ser Gln Val Ser Leu Val Ser Asn Gln Pro Val Thr Pro Arg Ser
            35                  40                  45

Ser Thr Met Asp Lys Gln Ser Leu Ser Leu Pro Asp Leu Met Ser Phe
        50                  55                  60

Gln Pro Gln Lys His Thr Leu Gly Pro Gly Thr Gly Thr Pro Glu Arg
65                  70                  75                  80

Ser Ser Ser Ser Ser Ser Ser Ser Ser Arg Arg Gly Glu Ala Ser
                85                  90                  95

Leu Asp Ala Thr Pro Ser Pro Glu Thr Thr Ser Leu Gln Thr Lys Lys
                100                 105                 110

Met Thr Ile Leu Leu Thr Ile Leu Pro Thr Pro Thr Ser Glu Ser Val
            115                 120                 125

Leu Thr Val Ala Ala Phe Gly Val Ile Ser Phe Ile Val Ile Leu Val
        130                 135                 140

Val Val Val Ile Ile Leu Val Ser Val Val Ser Leu Arg Phe Lys Cys
145                 150                 155                 160

Arg Lys Asn Lys Glu Ser Glu Asp Pro Gln Lys Pro Gly Ser Ser Gly
                165                 170                 175

Leu Ser Glu Ser Cys Ser Thr Ala Asn Gly Glu Lys Asp Ser Ile Thr
            180                 185                 190

Leu Ile Ser Met Arg Asn Ile Asn Val Asn Asn Ser Lys Gly Ser Met
            195                 200                 205

Ser Ala Glu Lys Ile Leu
        210

<210> SEQ ID NO 5
<211> LENGTH: 113
<212> TYPE: PRT
<213> ORGANISM: Mus musculus

<400> SEQUENCE: 5

Ser Gln Pro Thr Thr Thr Gln Thr Ser Gln Glu Ile Leu Gln Lys Ser
1               5                   10                  15

Ser Gln Val Ser Leu Val Ser Asn Gln Pro Val Thr Pro Arg Ser Ser
            20                  25                  30

Thr Met Asp Lys Gln Ser Leu Ser Leu Pro Asp Leu Met Ser Phe Gln
        35                  40                  45

Pro Gln Lys His Thr Leu Gly Pro Gly Thr Gly Thr Pro Glu Arg Ser
    50                  55                  60

Ser Ser Ser Ser Ser Ser Ser Ser Arg Arg Gly Glu Ala Ser Leu
65                  70                  75                  80

Asp Ala Thr Pro Ser Pro Glu Thr Thr Ser Leu Gln Thr Lys Lys Met
                85                  90                  95

Thr Ile Leu Leu Thr Ile Leu Pro Thr Pro Thr Ser Glu Ser Val Leu
            100                 105                 110

Thr

<210> SEQ ID NO 6
<211> LENGTH: 84
<212> TYPE: PRT
<213> ORGANISM: Mus musculus

<400> SEQUENCE: 6

| Val | Ala | Ala | Phe | Gly | Val | Ile | Ser | Phe | Ile | Val | Leu | Val | Val | Val |
|-----|-----|-----|-----|-----|-----|-----|-----|-----|-----|-----|-----|-----|-----|-----|
| 1 | | | | 5 | | | | | 10 | | | | | 15 |

| Val | Ile | Ile | Leu | Val | Ser | Val | Val | Ser | Leu | Arg | Phe | Lys | Cys | Arg | Lys |
|-----|-----|-----|-----|-----|-----|-----|-----|-----|-----|-----|-----|-----|-----|-----|-----|
| | | | 20 | | | | | 25 | | | | | 30 | | |

| Asn | Lys | Glu | Ser | Glu | Asp | Pro | Gln | Lys | Pro | Gly | Ser | Ser | Gly | Leu | Ser |
|-----|-----|-----|-----|-----|-----|-----|-----|-----|-----|-----|-----|-----|-----|-----|-----|
| | | 35 | | | | | 40 | | | | | 45 | | | |

| Glu | Ser | Cys | Ser | Thr | Ala | Asn | Gly | Glu | Lys | Asp | Ser | Ile | Thr | Leu | Ile |
|-----|-----|-----|-----|-----|-----|-----|-----|-----|-----|-----|-----|-----|-----|-----|-----|
| | 50 | | | | 55 | | | | | 60 | | | | | |

| Ser | Met | Arg | Asn | Ile | Asn | Val | Asn | Asn | Ser | Lys | Gly | Ser | Met | Ser | Ala |
|-----|-----|-----|-----|-----|-----|-----|-----|-----|-----|-----|-----|-----|-----|-----|-----|
| 65 | | | | 70 | | | | | 75 | | | | | 80 | |

Glu Lys Ile Leu

<210> SEQ ID NO 7
<211> LENGTH: 914
<212> TYPE: DNA
<213> ORGANISM: Homo sapiens
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t

<400> SEQUENCE: 7

```
gagcctccac tgagctgctg cctgcccgcc acatacccag ctgacatggg caccgcagga    60
gccatgcagc tgtgctgggt gatcctgggc ttcctcctgt tccgaggcca caactcccag   120
cccacaatga cccagacctc tagctctcag ggaggccttg gcggtctaag tctgaccaca   180
gagccagttt cttccaaccc aggatacatc ccttcctcag aggctaacag gccaagccat   240
ctgtccagca ctggtacccc aggcgcaggt gtccccagca gtggaagaga cggaggcaca   300
agcagagaca catttcaaac tgttcccccc aattcaacca ccatgagcct gagcatgagg   360
gaagatgcga ccatcctgcc cagccccacg tcagagactg tgctcactgt ggctgcattt   420
ggtgttatca gcttcattgt catcctggtg gttgtggtga tcatcctagt ggtgtggtc    480
agcctgaggt tcaagtgtcg gaagagcaag gagtctgaag atccccagaa acctgggagt   540
tcagggctgt ctgaaagctg ctccacagcc aatggagaga agacagcat caccccttatc   600
tccatgaaga acatcaacat gaataatggc aaacaaagtc tctcagcaga gaaggttctt   660
tanaagcaac tttgggtccc catgagtcca aggatgatgc agctgccctg tgactacaag   720
gaggaagaga tggaattagt agaggcaatg aaccacatgt aaattatttt attgtttcat   780
gtctgcttct agatctanag gacactagca ttgccccaga tctggggagc agctaccaac   840
agggggagac tctttttcctg tatggacagc tgctgtggaa atactggcc tggcttctcc    900
ccactcctca gagc                                                     914
```

<210> SEQ ID NO 8
<211> LENGTH: 291
<212> TYPE: DNA
<213> ORGANISM: Homo sapiens

<400> SEQUENCE: 8

```
cagcccacaa tgacccagac ctctagctct caggaggcc ttggcggtct aagtctgacc    60
acagagccag tttcttccaa cccaggatac atcccttcct cagaggctaa caggccaagc   120
```

```
catctgtcca gcactggtac cccaggcgca ggtgtcccca gcagtggaag agacggaggc      180
acaagcagag acacatttca aactgttccc cccaattcaa ccaccatgag cctgagcatg      240
agggaagatg cgaccatcct gcccagcccc acgtcagaga ctgtgctcac t              291
```

<210> SEQ ID NO 9
<211> LENGTH: 381
<212> TYPE: DNA
<213> ORGANISM: Homo sapiens
<220> FEATURE:
<221> NAME/KEY: misc_feature
<222> LOCATION: (255)..(255)
<223> OTHER INFORMATION: n is a, c, g, or t

<400> SEQUENCE: 9

```
gtggctgcat ttggtgttat cagcttcatt gtcatcctgg tggttgtggt gatcatccta       60
gttggtgtgg tcagcctgag gttcaagtgt cggaagagca aggagtctga agatccccag      120
aaacctggga gttcagggct gtctgaaagc tgctccacag ccaatggaga gaaagacagc      180 atcacccta tctccatgaa gaacatcaac atgaataatg gcaaacaaag tctctcagca       240
gagaaggttc tttanaagca actttgggtc cccatgagtc caaggatgat gcagctgccc      300
tgtgactaca aggaggaaga gatggaatta gtagaggcaa tgaaccacat gtaaattatt      360
ttattgtttc atgtctgctt c                                                381
```

<210> SEQ ID NO 10
<211> LENGTH: 205
<212> TYPE: PRT
<213> ORGANISM: Homo sapiens

<400> SEQUENCE: 10

```
Met Gly Thr Ala Gly Ala Met Gln Leu Cys Trp Val Ile Leu Gly Phe
1               5                   10                  15

Leu Leu Phe Arg Gly His Asn Ser Gln Pro Thr Met Thr Gln Thr Ser
            20                  25                  30

Ser Ser Gln Gly Gly Leu Gly Gly Leu Ser Leu Thr Thr Glu Pro Val
        35                  40                  45

Ser Ser Asn Pro Gly Tyr Ile Pro Ser Ser Glu Ala Asn Arg Pro Ser
    50                  55                  60

His Leu Ser Ser Thr Gly Thr Pro Gly Ala Gly Val Pro Ser Ser Gly
65                  70                  75                  80

Arg Asp Gly Gly Thr Ser Arg Asp Thr Phe Gln Thr Val Pro Pro Asn
                85                  90                  95

Ser Thr Thr Met Ser Leu Ser Met Arg Glu Asp Ala Thr Ile Leu Pro
            100                 105                 110

Ser Pro Thr Ser Glu Thr Val Leu Thr Val Ala Ala Phe Gly Val Ile
        115                 120                 125

Ser Phe Ile Val Ile Leu Val Val Val Ile Ile Leu Val Gly Val
    130                 135                 140

Val Ser Leu Arg Phe Lys Cys Arg Lys Ser Lys Glu Ser Glu Asp Pro
145                 150                 155                 160

Gln Lys Pro Gly Ser Ser Gly Leu Ser Glu Ser Cys Ser Thr Ala Asn
                165                 170                 175

Gly Glu Lys Asp Ser Ile Thr Leu Ile Ser Met Lys Asn Ile Asn Met
            180                 185                 190

Asn Asn Gly Lys Gln Ser Leu Ser Ala Glu Lys Val Leu
        195                 200                 205
```

-continued

```
           195                 200                 205
```

<210> SEQ ID NO 11
<211> LENGTH: 97
<212> TYPE: PRT
<213> ORGANISM: Homo sapiens

<400> SEQUENCE: 11

```
Gln Pro Thr Met Thr Gln Thr Ser Ser Gln Gly Gly Leu Gly Gly
1               5                  10                  15

Leu Ser Leu Thr Thr Glu Pro Val Ser Ser Asn Pro Gly Tyr Ile Pro
                20                  25                  30

Ser Ser Glu Ala Asn Arg Pro Ser His Leu Ser Ser Thr Gly Thr Pro
            35                  40                  45

Gly Ala Gly Val Pro Ser Ser Gly Arg Asp Gly Thr Ser Arg Asp
        50                  55                  60

Thr Phe Gln Thr Val Pro Pro Asn Ser Thr Met Ser Leu Ser Met
65                  70                  75                  80

Arg Glu Asp Ala Thr Ile Leu Pro Ser Pro Thr Ser Glu Thr Val Leu
                85                  90                  95

Thr
```

<210> SEQ ID NO 12
<211> LENGTH: 84
<212> TYPE: PRT
<213> ORGANISM: Homo sapiens

<400> SEQUENCE: 12

```
Val Ala Ala Phe Gly Val Ile Ser Phe Ile Val Ile Leu Val Val Val
1               5                  10                  15

Val Ile Ile Leu Val Gly Val Val Ser Leu Arg Phe Lys Cys Arg Lys
                20                  25                  30

Ser Lys Glu Ser Glu Asp Pro Gln Lys Pro Gly Ser Ser Gly Leu Ser
            35                  40                  45

Glu Ser Cys Ser Thr Ala Asn Gly Glu Lys Asp Ser Ile Thr Leu Ile
        50                  55                  60

Ser Met Lys Asn Ile Asn Met Asn Asn Gly Lys Gln Ser Leu Ser Ala
65                  70                  75                  80

Glu Lys Val Leu
```

<210> SEQ ID NO 13
<211> LENGTH: 716
<212> TYPE: DNA
<213> ORGANISM: Bos taurus

<400> SEQUENCE: 13

```
acagaggctg cctgccggtt gcagaccaag ctgacatggg gagtgtcaga gaaacgcagc      60
tgcgctgggc catcctgggc ttcctcctgc tccaaggagc cttcagcagt caaagttcaa     120
ccacacagcc agcttcccct gaaacaagtc cttccacaga ggccaacagc ttaagccctc     180
tgtccggcac ctggaccaca gcagcatcag agacgccctc acagttctcc acggaagcca     240
tgactctgag ttcaagcacc gtggctgatc acttgccgtc ctctccggga ccgacttggt     300
cccagtcaca gaaacacacg tcaggactca gcgctgatgt tccgagcagt ggcaggagca     360
gcgacagcat gagtggagac acctctcaca atgttacttc cacatcaccc aacatgagtt     420
ttaggacgac agcagactcc actgtcccac ccagccccac gtcagagacg gtgctcactg     480
```

```
tggctgcatt tggtgttatc agcttcattg ccatcctagt ggttgtggtg attgtcctgg      540
tcagtgtggt cagtctaagg tttaagtgtc ggaagaacaa ggagtctgaa gatccccaga      600
aacctgggag ttcagggctc tctgaaagcg gttccacagc caatggagag aaagagagca      660
tcactcttat ctcgatgaag aacatcaaca tgaataacag caaggatgc ccctca           716
```

```
<210> SEQ ID NO 14
<211> LENGTH: 369
<212> TYPE: DNA
<213> ORGANISM: Bos taurus

<400> SEQUENCE: 14
caaagttcaa ccacacagcc agcttcccct gaaacaagtc cttccacaga ggccaacagc       60
ttaagccctc tgtccggcac ctggaccaca gcagcatcag agacgccctc acagttctcc      120
acggaagcca tgactctgag ttcaagcacc gtggctgatc acttgccgtc ctctccggga      180
ccgacttggt cccagtcaca gaaacacacg tcaggactca gcgctgatgt tccgagcagt      240
ggcaggagca gcgacagcat gagtggagac acctctcaca atgttacttc cacatcaccc      300
aacatgagtt taggacgac agcagactcc actgtcccac ccagccccac gtcagagacg       360
gtgctcact                                                              369
```

```
<210> SEQ ID NO 15
<211> LENGTH: 237
<212> TYPE: DNA
<213> ORGANISM: Bos taurus

<400> SEQUENCE: 15
gtggctgcat tggtgttat cagcttcatt gccatcctag tggttgtggt gattgtcctg        60
gtcagtgtgg tcagtctaag gtttaagtgt cggaagaaca aggagtctga agatccccag      120
aaacctggga gttcagggct ctctgaaagc ggttccacag ccaatggaga aagagagc        180 atcactctta tctcgatgaa gaacatcaac atgaataaca gcaaggatg ccccctca         237
```

```
<210> SEQ ID NO 16
<211> LENGTH: 240
<212> TYPE: PRT
<213> ORGANISM: Bos taurus

<400> SEQUENCE: 16

Arg Gly Cys Leu Pro Val Ala Asp Gln Ala Asp Met Gly Ser Val Arg
1               5                   10                  15

Glu Thr Gln Leu Arg Trp Ala Ile Leu Gly Phe Leu Leu Gln Gly
            20                  25                  30

Ala Phe Ser Ser Gln Ser Ser Thr Gln Pro Ala Ser Pro Glu Thr
        35                  40                  45

Ser Pro Ser Thr Glu Ala Asn Ser Leu Ser Pro Leu Ser Gly Thr Trp
    50                  55                  60

Thr Thr Ala Ala Ser Glu Thr Pro Ser Gln Phe Ser Thr Glu Ala Met
65                  70                  75                  80

Thr Leu Ser Ser Ser Thr Val Ala Asp His Leu Pro Ser Ser Pro Gly
                85                  90                  95

Pro Thr Trp Ser Gln Ser Gln Lys His Thr Ser Gly Leu Ser Ala Asp
            100                 105                 110

Val Pro Ser Ser Gly Arg Ser Ser Asp Ser Met Ser Gly Asp Thr Ser
        115                 120                 125
```

```
His Asn Val Thr Ser Thr Ser Pro Asn Met Ser Phe Arg Thr Thr Ala
    130                 135                 140

Asp Ser Thr Val Pro Pro Ser Pro Thr Ser Glu Thr Val Leu Thr Val
145                 150                 155                 160

Ala Ala Phe Gly Val Ile Ser Phe Ile Ala Ile Leu Val Val Val Val
                165                 170                 175

Thr Ile Val Leu Val Ser Val Val Ser Leu Arg Phe Lys Cys Arg Lys
                180                 185                 190

Asn Lys Glu Ser Glu Asp Pro Gln Lys Pro Gly Ser Ser Gly Leu Ser
                195                 200                 205

Glu Ser Gly Ser Thr Ala Asn Gly Glu Lys Glu Ser Ile Thr Leu Ile
                210                 215                 220

Ser Met Lys Asn Ile Ile Asn Met Asn Asn Ser Lys Gly Cys Pro Ser
225                 230                 235                 240

<210> SEQ ID NO 17
<211> LENGTH: 124
<212> TYPE: PRT
<213> ORGANISM: Bos taurus

<400> SEQUENCE: 17

Ser Gln Ser Ser Thr Thr Gln Pro Ala Ser Pro Glu Thr Ser Pro Ser
1               5                   10                  15

Thr Glu Ala Asn Ser Leu Ser Pro Leu Ser Gly Thr Trp Thr Thr Ala
                20                  25                  30

Ala Ser Glu Thr Pro Ser Gln Phe Ser Thr Glu Ala Met Thr Leu Ser
                35                  40                  45

Ser Ser Thr Val Ala Asp His Leu Pro Ser Ser Pro Gly Pro Thr Trp
            50                  55                  60

Ser Gln Ser Gln Lys His Thr Ser Gly Leu Ser Ala Asp Val Pro Ser
65              70                  75                  80

Ser Gly Arg Ser Ser Asp Ser Met Ser Gly Asp Thr Ser His Asn Val
                85                  90                  95

Thr Ser Thr Ser Pro Asn Met Ser Phe Arg Thr Thr Ala Asp Ser Thr
                100                 105                 110

Val Pro Pro Ser Pro Thr Ser Glu Thr Val Leu Thr
            115                 120

<210> SEQ ID NO 18
<211> LENGTH: 81
<212> TYPE: PRT
<213> ORGANISM: Bos taurus

<400> SEQUENCE: 18

Val Ala Ala Phe Gly Val Ile Ser Phe Ile Ala Ile Leu Val Val Val
1               5                   10                  15

Val Thr Ile Val Leu Val Ser Val Val Ser Leu Arg Phe Lys Cys Arg
                20                  25                  30

Lys Asn Lys Glu Ser Glu Asp Pro Gln Lys Pro Gly Ser Ser Gly Leu
                35                  40                  45

Ser Glu Ser Gly Ser Thr Ala Asn Gly Glu Lys Glu Ser Ile Thr Leu
            50                  55                  60

Ile Ser Met Lys Asn Ile Ile Asn Met Asn Asn Ser Lys Gly Cys Pro
65                  70                  75                  80

Ser
```

```
<210> SEQ ID NO 19
<211> LENGTH: 549
<212> TYPE: DNA
<213> ORGANISM: Sus scrofa

<400> SEQUENCE: 19
ccacgcgtcc gcgccagcct gccccgtccc actgacatgg ggagcgtcgg agaaacgcag      60
ctgtgctggg ccatcctggg cttcctcctg ctccaaggcc acggctccca gctcacaata     120
cctagccctc agggagagag tccttccgca gagtccaaca gctcaagccc tctatccagc     180
agcaccagca gcagcagcaa cagcagcagc agcaccagca ccacagacac ccctcacaat     240
ggtacgtcca cgtcacccac cgtgagtctg agaaccagag aagacccgac cgtcctgccc     300
agccccacgt cagagacggt gctcacagtg gccgcctttg gtgtcatcag cttcattgtc     360
atcctgctgg ttgtggtgat catcctggtc agcgtggtca gtctaaggtt taagtgtcgg     420
aggaacaagg aatctgaaga tccccagaaa cctgggagtt cggggctctc tgaaagctgc     480
tccacagcca atggagagaa agacagcatc accctcatct ccatgaaaaa tatcaacatg     540
aataacagc                                                              549

<210> SEQ ID NO 20
<211> LENGTH: 219
<212> TYPE: DNA
<213> ORGANISM: Sus scrofa

<400> SEQUENCE: 20
cagctcacaa tacctagccc tcagggagag agtccttccg cagagtccaa cagctcaagc      60
cctctatcca gcagcaccag cagcagcagc aacagcagca gcagcaccag caccacagac     120 accccctcaca atggtacgtc cacgtcaccc accgtgagtc tgagaaccag agaagacccg     180
accgtcctgc ccagccccac gtcagagacg gtgctcaca                             219

<210> SEQ ID NO 21
<211> LENGTH: 222
<212> TYPE: DNA
<213> ORGANISM: Sus scrofa

<400> SEQUENCE: 21
gtggccgcct ttggtgtcat cagcttcatt gtcatcctgc tggttgtggt gatcatcctg      60
gtcagcgtgg tcagtctaag gtttaagtgt cggaggaaca aggaatctga agatccccag     120
aaacctggga gttcggggct ctctgaaagc tgctccacag ccaatggaga gaaagacagc     180
atcaccctca tctccatgaa aaatatcaac atgaataaca gc                         222

<210> SEQ ID NO 22
<211> LENGTH: 183
<212> TYPE: PRT
<213> ORGANISM: Sus scrofa

<400> SEQUENCE: 22

Pro Arg Val Arg Ala Ser Leu Pro Arg Pro Thr Asp Met Gly Ser Val
1               5                   10                  15

Gly Glu Thr Gln Leu Cys Trp Ala Ile Leu Gly Phe Leu Leu Leu Gln
                20                  25                  30

Gly His Gly Ser Gln Leu Thr Ile Pro Ser Pro Gln Gly Glu Ser Pro
            35                  40                  45

Ser Ala Glu Ser Asn Ser Ser Ser Pro Leu Ser Ser Ser Thr Ser Ser
        50                  55                  60
```

```
Ser Ser Asn Ser Ser Ser Thr Ser Thr Thr Asp Thr Pro His Asn
 65                  70                  75                  80

Gly Thr Ser Thr Ser Pro Thr Val Ser Leu Arg Thr Arg Glu Asp Pro
                 85                  90                  95

Thr Val Leu Pro Ser Pro Thr Ser Glu Thr Val Leu Thr Val Ala Ala
            100                 105                 110

Phe Gly Val Ile Ser Phe Ile Val Ile Leu Leu Val Val Ile Ile
            115                 120                 125

Leu Val Ser Val Val Ser Leu Arg Phe Lys Cys Arg Arg Asn Lys Glu
130                 135                 140

Ser Glu Asp Pro Gln Lys Pro Gly Ser Ser Gly Leu Ser Glu Ser Cys
145                 150                 155                 160

Ser Thr Ala Asn Gly Glu Lys Asp Ser Ile Thr Leu Ile Ser Met Lys
                165                 170                 175

Asn Ile Asn Met Asn Asn Ser
            180
```

<210> SEQ ID NO 23
<211> LENGTH: 73
<212> TYPE: PRT
<213> ORGANISM: Sus scrofa

<400> SEQUENCE: 23

```
Gln Leu Thr Ile Pro Ser Pro Gln Gly Glu Ser Pro Ser Ala Glu Ser
  1               5                  10                  15

Asn Ser Ser Pro Leu Ser Ser Thr Ser Ser Ser Asn Ser
             20                  25                  30

Ser Ser Ser Thr Ser Thr Thr Asp Thr Pro His Asn Gly Thr Ser Thr
             35                  40                  45

Ser Pro Thr Val Ser Leu Arg Thr Arg Glu Asp Pro Thr Val Leu Pro
 50                  55                  60

Ser Pro Thr Ser Glu Thr Val Leu Thr
 65                  70
```

<210> SEQ ID NO 24
<211> LENGTH: 74
<212> TYPE: PRT
<213> ORGANISM: Sus scrofa

<400> SEQUENCE: 24

```
Val Ala Ala Phe Gly Val Ile Ser Phe Ile Val Ile Leu Leu Val Val
  1               5                  10                  15

Val Ile Ile Leu Val Ser Val Val Ser Leu Arg Phe Lys Cys Arg Arg
             20                  25                  30

Asn Lys Glu Ser Glu Asp Pro Gln Lys Pro Gly Ser Ser Gly Leu Ser
             35                  40                  45

Glu Ser Cys Ser Thr Ala Asn Gly Glu Lys Asp Ser Ile Thr Leu Ile
 50                  55                  60

Ser Met Lys Asn Ile Asn Met Asn Asn Ser
 65                  70
```

<210> SEQ ID NO 25
<211> LENGTH: 1104
<212> TYPE: DNA
<213> ORGANISM: Mus musculus

<400> SEQUENCE: 25
atgaggctgg gttcagcaat tctcggttta ctcctgctcc aaggctacag ctctcaacct     60

-continued

```
acgacaactc agacctcgca ggaaattcta cagaagtctt ctcaggtctc cttggtatcc    120
aatcagcctg tgacaccaag gtcaagcacc atggataaac agtccctttc cttgcctgac    180
ttgatgtcct tccagccaca gaagcacaca ctgggacctg gcacaggaac cccagaaagg    240
agcagcagca gcagcagcag cagcagcagc aggagaggag aagcatctct ggatgctact    300
cccagtccag aaaccaccag ccttcagaca aaaagatga ccatcctgct gaccatcctg    360
cctaccccca catcagagtc agtgctaact ggtaccggac caggagagcc caaatcttgt    420
gacaaaactc acacatgccc accgtgccca gcacctgaac tcctgggggg accgtcagtc    480
ttcctcttcc ccccaaaacc caaggacacc ctcatgatct cccggacccc tgaggtcaca    540
tgcgtggtgg tggacgtgag ccacgaagac cctgaggtca agttcaactg gtacgtggac    600
ggcgtggagg tgcataatgc caagacaaag ccgcgggagg agcagtacaa cagcacgtac    660
cgtgtggtca gcgtcctcac cgtcctgcac caggactggc tgaatggcaa ggagtacaag    720
tgcaaggtct ccaacaaagc cctcccagcc cccatcgaga aaaccatctc caaagccaaa    780
gggcagcccc gagaaccaca ggtgtacacc ctgcccccat cccgggagga tgaccaag    840 aaccaggtca gcctgacctg cctggtcaaa ggcttctatc ccagcgacat cgccgtggag    900
tgggagagca atgggcagcc ggagaacaac tacaagacca cgcctcccgt gctggactcc    960
gacggctcct tcttcctcta cagcaagctc accgtggaca agagcaggtg gcagcagggg   1020
aacgtcttct catgctccgt gatgcatgag gctctgcaca accactacac gcagaagagc   1080
ctctccctgt ctccgggtaa atga                                         1104
```

<210> SEQ ID NO 26
<211> LENGTH: 367
<212> TYPE: PRT
<213> ORGANISM: Mus musculus

<400> SEQUENCE: 26

```
Met Arg Leu Gly Ser Ala Ile Leu Gly Leu Leu Leu Gln Gly Tyr
1               5                   10                  15

Ser Ser Gln Pro Thr Thr Thr Gln Thr Ser Gln Glu Ile Leu Gln Lys
                20                  25                  30

Ser Ser Gln Val Ser Leu Val Ser Asn Gln Pro Val Thr Pro Arg Ser
            35                  40                  45

Ser Thr Met Asp Lys Gln Ser Leu Ser Leu Pro Asp Leu Met Ser Phe
        50                  55                  60

Gln Pro Gln Lys His Thr Leu Gly Pro Gly Thr Gly Thr Pro Glu Arg
65                  70                  75                  80

Ser Ser Ser Ser Ser Ser Ser Ser Arg Arg Gly Glu Ala Ser
                85                  90                  95

Leu Asp Ala Thr Pro Ser Pro Glu Thr Thr Ser Leu Gln Thr Lys Lys
                100                 105                 110

Met Thr Ile Leu Leu Thr Ile Leu Pro Thr Pro Thr Ser Glu Ser Val
            115                 120                 125

Leu Thr Gly Thr Gly Pro Gly Glu Pro Lys Ser Cys Asp Lys Thr His
        130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
```

```
                180             185             190
Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
        210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
                260                 265                 270

Pro Ser Arg Glu Glu Met Thr Lys Asn Gln Val Ser Leu Thr Cys Leu
        275                 280                 285

Val Lys Gly Phe Tyr Pro Ser Asp Ile Ala Val Glu Trp Glu Ser Asn
290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
                340                 345                 350

His Asn His Tyr Thr Gln Lys Ser Leu Ser Leu Ser Pro Gly Lys
        355                 360                 365

<210> SEQ ID NO 27
<211> LENGTH: 1122
<212> TYPE: DNA
<213> ORGANISM: Homo sapiens

<400> SEQUENCE: 27
gagcctccac tgagctgctg cctgcccgcc acatacccag ctgacatggg caccgcagga     60
gccatgcagc tgtgctgggt gatcctgggc ttcctcctgt ccgaggccca aactcccag    120 cccacaatga cccagaccct cagctctcag gaggccttg gcggtctaag tctgaccaca    180
gagccagttt cttccaaccc aggatacatc ccttcctcag aggctaacag gccaagccat    240
ctgtccagca ctggtacccc aggcgcaggt gtccccagca gtggaagaga cggaggcaca    300
agcagagaca catttcaaac tgttcccccc aattcaacca ccatgagcct gagcatgagg    360
gaagatgcga ccatcctgcc cagccccacg tcagagactg tgctcactgg taccggacca    420
ggagagccca atcttgtgca aaaactcac acatgcccac cgtgcccagc acctgaactc    480
ctggggggac cgtcagtctt cctcttcccc ccaaaaccca aggacaccct catgatctcc    540
cggacccctg aggtcacatg cgtggtggtg gacgtgagcc acgaagaccc tgaggtcaag    600
ttcaactggt acgtggacgg cgtggaggtg cataatgcca agacaaagcc gcgggaggag    660
cagtacaaca gcacgtaccg tgtggtcagc gtcctcaccg tcctgcacca ggactggctg    720
aatggcaagg agtacaagtg caaggtctcc aacaaagccc tcccagcccc catcgagaaa    780
accatctcca aagccaaagg gcagcccga gaaccacagg tgtacaccct gcccccatcc    840
cgggaggaga tgaccaagaa ccaggtcagc ctgacctgcc tggtcaaagg cttctatccc    900
agcgacatcg ccgtggagtg ggagagcaat gggcagccgg agaacaacta caagaccacg    960
```

```
cctcccgtgc tggactccga cggctccttc ttcctctaca gcaagctcac cgtggacaag    1020
agcaggtggc agcagggaa cgtcttctca tgctccgtga tgcatgaggc tctgcacaac     1080
cactacacgc agaagagcct ctccctgtct ccgggtaaat ga                       1122
```

<210> SEQ ID NO 28
<211> LENGTH: 334
<212> TYPE: PRT
<213> ORGANISM: Homo sapiens

<400> SEQUENCE: 28

```
Gln Pro Thr Met Thr Gln Thr Ser Ser Ser Gln Gly Gly Leu Gly Gly
1               5                   10                  15

Leu Ser Leu Thr Thr Glu Pro Val Ser Ser Asn Pro Gly Tyr Ile Pro
            20                  25                  30

Ser Ser Glu Ala Asn Arg Pro Ser His Leu Ser Ser Thr Gly Thr Pro
        35                  40                  45

Gly Ala Gly Val Pro Ser Ser Gly Arg Asp Gly Gly Thr Ser Arg Asp
    50                  55                  60

Thr Phe Gln Thr Val Pro Pro Asn Ser Thr Thr Met Ser Leu Ser Met
65                  70                  75                  80

Arg Glu Asp Ala Thr Ile Leu Pro Ser Pro Thr Ser Glu Thr Val Leu
                85                  90                  95

Thr Gly Thr Gly Pro Gly Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330
```

METHOD FOR INHIBITING ANGIOGENESIS BY ADMINISTRATION OF THE EXTRACELLULAR DOMAIN OF D1-1 POLYPEPTIDE

RELATED APPLICATIONS

This application claims the benefit of the filing date of U.S. Provisional Application No. 60/375,904, filed Apr. 26, 2002, and incorporated by reference herein in its entirety.

FUNDING

Work described herein was funded, in whole or in part, by National Heart, Lung, and Blood Institute (NHLBI) Grant No. HL66221. The United States government has certain rights in the invention.

BACKGROUND

Angiogenesis, the process of forming new blood vessels, is critical in many normal and abnormal physiological states. Under normal physiological conditions, humans or animals undergo angiogenesis in specific and restricted situations. For example, angiogenesis is normally observed in wound healing, fetal and embryonic development and formation of the corpus luteum, endometrium and placenta.

Undesirable or inappropriately regulated angiogenesis occurs in a many disorders, in which abnormal endothelial growth may cause or participate in the pathological process. For example, abnormal endothelial cell proliferation has been postulated to contribute to atherosclerosis. Angiogenesis also participates in the growth of many tumors. Deregulated angiogenesis has been implicated in pathological processes such as rheumatoid arthritis, retinopathies, hemangiomas, and psoriasis. The diverse pathological disease states in which unregulated angiogenesis is present have been categorized as angiogenesis-dependent or angiogenesis-associated diseases.

Inadequate angiogenesis is implicated in several diseases and biological processes. Inadequate vascularization of the uterine endometrium and associated infertility, wound repair, healing of cuts and incisions, are some of the examples of problems caused by or associated with inadequate angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" protruding from the parent blood vessel, where the endothelial cells undergo mitosis and proliferate. Endothelial sprouts merge with each other to form capillary loops, creating the new blood vessel.

What is needed therefore are compositions and methods which can modulate angiogenesis according to specific situations. These include methods and compositions which can inhibit the unwanted growth of blood vessels, especially blood vessels that support tumor growth. Furthermore, it is also desirable to have methods and compositions which can promote angiogenesis to treat inadequate angiogenesis in certain diseases and processes.

SUMMARY

In certain aspects, the present invention features a family of proteins, D1-1 proteins, that are novel Type I transmembrane proteins involved in angiogenesis, and nucleic acids encoding D1-1 proteins. In certain embodiments of the present invention provides D1-1 proteins and nucleic acids from a variety of different species, as well as variants, including fragments and fusion proteins. In certain embodiments, the invention provides truncated extracellular D1-1 polypeptides, optionally engineered to be fusion proteins comprising a heterologous polypeptide, such as an Fc domain, and in certain embodiments, such polypeptides may be used as inhibitors of angiogenesis. In certain aspects, the invention provides methods, compositions and new model systems for manipulating angiogenesis and diseases involving angiogenic disorders. In certain aspects, the invention provides screening methods for identifying therapeutic agents useful for the prevention or the treatment of angiogenesis-related disorders.

An aspect of the invention provides D1-1 polypeptides and fragments thereof. An aspect of the invention encompasses truncated extracellular D1-1 polypeptides and derivatives thereof, especially angiogenesis-inhibiting peptide fragments. The truncated extracellular D1-1 fragments can be provided as a fusion protein which includes a second polypeptide portion, e.g. the second polypeptide having an amino acid sequence unrelated (heterologous) to D1-1. For example, the heterologous polypeptide portion may include a multimerization domain (e.g. a dimerization, trimerization or tetramerization domain), a stabilizing domain (e.g. a domain that stabilizes or aids in the solubility of the fusion protein), a targeting domain (e.g. a domain that targets the fusion protein to a particular cell or tissue type) and a purification domain (e.g. a domain that facilitates purification of the fusion protein). For example, the second polypeptide portion may be the Fc portion of an immunoglobulin, or glutathione-S-transferase, or an enzymatic activity such as alkaline phosphatase, or an epitope tag. The invention also includes D1-1 antibody, D1-1 ligands, D1-1 agonists or antagonists and other D1-1 associated proteins.

An aspect of the invention provides nucleic acid sequences that code for D1-1 amino acid sequences, and complementary sequences thereof. In certain embodiments, nucleic acids of the invention encode angiogenesis-inhibiting D1-1 polypeptides. In certain embodiments, the invention also includes antibodies directed against D1-1 or fragments thereof. In specific embodiments, the invention includes antibodies directed against an extracellular region, or an intracellular region of the D1-1 protein.

Another aspect of the invention provides for a non-human transgenic animal comprising a mutation in the D1-1 gene. In a specific embodiment, the mutation is a deletion. The mutation may affect one allele or both alleles. In a specific embodiment, the animal is a rodent and preferably a mouse. In certain embodiments, the transgenic animals according to the invention provide model systems for studying angiogenesis associated diseases and for screening and/or testing agents useful for treating and/or preventing these diseases. Organs from the transgenic animals (such as retina, aortas, etc.) are useful for screening and/or testing such agents. Cells from the transgenic animals are also useful for screening and/or testing such agents.

It is yet another aspect of the present invention to provide methods and compositions for treating angiogenesis-associated diseases, processes and other pathologies in which D1-1 is involved. An important example of an angiogenesis-associated disease is cancer.

In certain embodiments, the invention provides methods and compositions for treating diseases and processes mediated by undesired and uncontrolled angiogenesis by administering to a human or animal a composition comprising a substantially purified truncated extracellular D1-1 polypeptides in a dosage sufficient to inhibit angiogenesis. In certain aspects, the methods and compositions may be used for treating or repressing the growth of tumors, and particularly prevascularized tumors. The method also relates to the co-administration of the truncated extracellular D1-1 polypeptides of the present invention and another anti-angiogenesis compound, for example, angiostatin or endostatin. In certain embodiments, the invention provides a new form of birth control, wherein an effective amount of truncated extracellular D1-1 is administrated to a female subject such that uterine endometrial vascularization is inhibited and embryo implantation cannot occur, or be sustained.

In certain aspects, the invention also features methods and compositions that may promote endothelialization and vascularization. Antagonists of the truncated extracellular D1-1 polypeptides with angiogenesis-inhibitory activity may act in such an angiogenesis-stimulating fashion. Accordingly, such agents will be useful in situations of inadequate vascularization of the uterine endometrium and associated infertility, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

In certain aspects, the present invention also includes diagnostic methods and kits for detecting D1-1 polypeptide in biological fluids. In certain aspects, the present invention also includes antibodies specific for D1-1 and antibodies that inhibit the binding of antibodies specific for D1-1. These antibodies can be polyclonal antibodies or monoclonal antibodies. The antibodies specific for the D1-1 can be used in diagnostic kits to detect the presence and quantity of D1-1 which may be diagnostic or prognostic for the occurrence or recurrence of cancer or other diseases mediated by angiogenesis. Antibodies specific for D1-1 may also be administered to a human or animal to passively immunize the human or animal against D1-1.

Another aspect of the invention includes diagnostic methods and kits for detecting the presence and quantity of antibodies that bind D1-1 in body fluids. The diagnostic method and kit can be in any configuration well known to those of ordinary skill in the art.

Angiogenesis-inhibiting agents can be given prophylactically to individuals known to be at high risk for developing new or re-current tumors or other disorders or conditions associated with unwanted angiogenesis. Accordingly, an aspect of the invention encompasses methods for prophylactic prevention of unwanted angiogenesis in a subject, comprising administering to the subject an effective amount of a truncated extracellular D1-1 polypeptide.

In certain aspects, the invention further includes methods for modulating angiogenesis in vivo, using the D1-1 protein or variants thereof, or nucleic acids corresponding to the D1-1 proteins and variants, or antibodies that bind specifically to the proteins of the present invention. Without limitations, these methods may, for example, comprise inhibiting expression of an endogenous D1-1 nucleic acid by contacting a cell expressing D1-1 with a siRNA, an antisense nucleic acid or a ribozyme. These methods may further comprise increasing D1-1 expression by causing a cell to express a heterologous D1-1 nucleic acid, and administrating to a subject at least o portion of D1-1 protein or variants thereof.

Another aspect of the invention provides methods for assessing the ability of an agent to bind to D1-1, comprising combining a polypeptide including at least a portion of D1-1 and an agent, and determining whether said agent binds to the said polypeptide. An agent that binds to D1-1 may be used to target reagents (e.g. labeling or cytotoxic agents) to D1-1 expressing cells, and such agents may also be further evaluated from pro- or anti-angiogenic effects.

A further aspect of the invention includes methods for assessing the ability of an agent to modulate angiogenesis, comprising: (1) combining a polypeptide including at least a portion of D1-1 and an agent under conditions wherein the polypeptide modulate angiogenesis in an angiogenesis assay in the absence of the agent, and (2) determining if the agent interferes with or promotes said modulation of angiogenesis. A significant increase in the angiogenesis activity indicates the agent to be an angiogenesis-enhancing agent, and a significant decrease in the angiogenesis activity indicates the agent to be an angiogenesis-inhibiting agent. Angiogenesis assays may include chick chorioallantoic membrane assay (CAM assay) and cornea assay, as explained in detail in the Examples.

Another aspect of the invention provides methods for assessing the ability of an agent to modulate angiogenesis, comprising: administering an agent to a transgenic animal comprising a mutation in D1-1 gene and comparing angiogenesis to that in untreated control animal.

Another aspect of the invention provides for a therapeutic agent capable of modulating angiogenesis. The agent of the invention can also be an antisense nucleic acid, a ribozyme, or a RNAi that is capable of down regulating or blocking expression of a D1-1 gene. In another embodiment, the agent of the invention can be a D1-1 associated protein, such as a natural ligand of the D1-1 protein. A D1-1 associated protein can bind to the intracellular or extracellular portion of the D1-1 protein. Yet in another embodiment, the agent of the invention can be a D1-1 dominant-negative mutant or a D1-1 constitutive mutant.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

FIG. 1. Alignment of murine, human, porcine and bovine D1-1 deduced amino acid sequences. Regions of identity are black. TM, transmembrane domain. Blue and magenta dots indicate putative sites of Serine or Threonine-linked O-glycosylation in the predicted extracellular domain, green dots indicate potential Serine phosphorylation sites in the predicted cytoplasmic domain.

FIG. 5A-C: Examples of murine D1-1 nucleic acid sequences, and those portions encoding extracellular or conserved portions of the D1-1 polypeptide. (SEQ ID Nos. 1-3). In 5A, the portion encoding the signal sequence is double underlined, and the portion encoding the extracellular portion (without the signal sequence) is single underlined.

FIG. 6A-C: Examples of murine D1-1 amino acid sequences, and the extracellular or conserved portions thereof. (SEQ ID Nos. 4-6). In 6A, the signal sequence is double underlined, and the extracellular portion (without the signal sequence) is single underlined.

FIG. 7A-C: Examples of human D1-1 nucleic acid sequences, and those portions encoding extracellular or conserved portions of the D1-1 polypeptide. (SEQ ID Nos. 7-9). In 7A, the portion encoding the signal sequence is double underlined, and the portion encoding the extracellular portion (without the signal sequence) is single underlined.

FIG. 8A-C: Examples of human D1-1 amino acid sequences, and the extracellular or conserved portions thereof. (SEQ ID Nos. 10-12). In 8A, the signal sequence is double underlined, and the extracellular portion (without the signal sequence) is single underlined.

FIG. 9A-C: Examples of bovine D1-1 nucleic acid sequences, and those portions encoding extracellular or conserved portions of the D1-1 polypeptide. (SEQ ID Nos. 13-15). In 9A, the portion encoding the signal sequence is double underlined, and the portion encoding the extracellular portion (without the signal sequence) is single underlined.

FIG. 10A-C: Examples of bovine D1-1 amino acid sequences, and the extracellular or conserved portions thereof. (SEQ ID Nos. 16-18). In 10A, the signal sequence is double underlined, and the extracellular portion (without the signal sequence) is single underlined.

FIG. 11A-C: Examples of bovine D1-1 nucleic acid sequences, and those portions encoding extracellular or conserved portions of the D1-1 polypeptide. (SEQ ID Nos. 19-21). In 11A, the portion encoding the signal sequence is double underlined, and the portion encoding the extracellular portion (without the signal sequence) is single underlined.

FIG. 12A-C: Examples of bovine D1-1 amino acid sequences, and the extracellular or conserved portions thereof. (SEQ ID Nos. 22-24). In 12A, the signal sequence is double underlined, and the extracellular portion (without the signal sequence) is single underlined.

DETAILED DESCRIPTION OF THE INVENTION

1. Definitions

Figure 2:
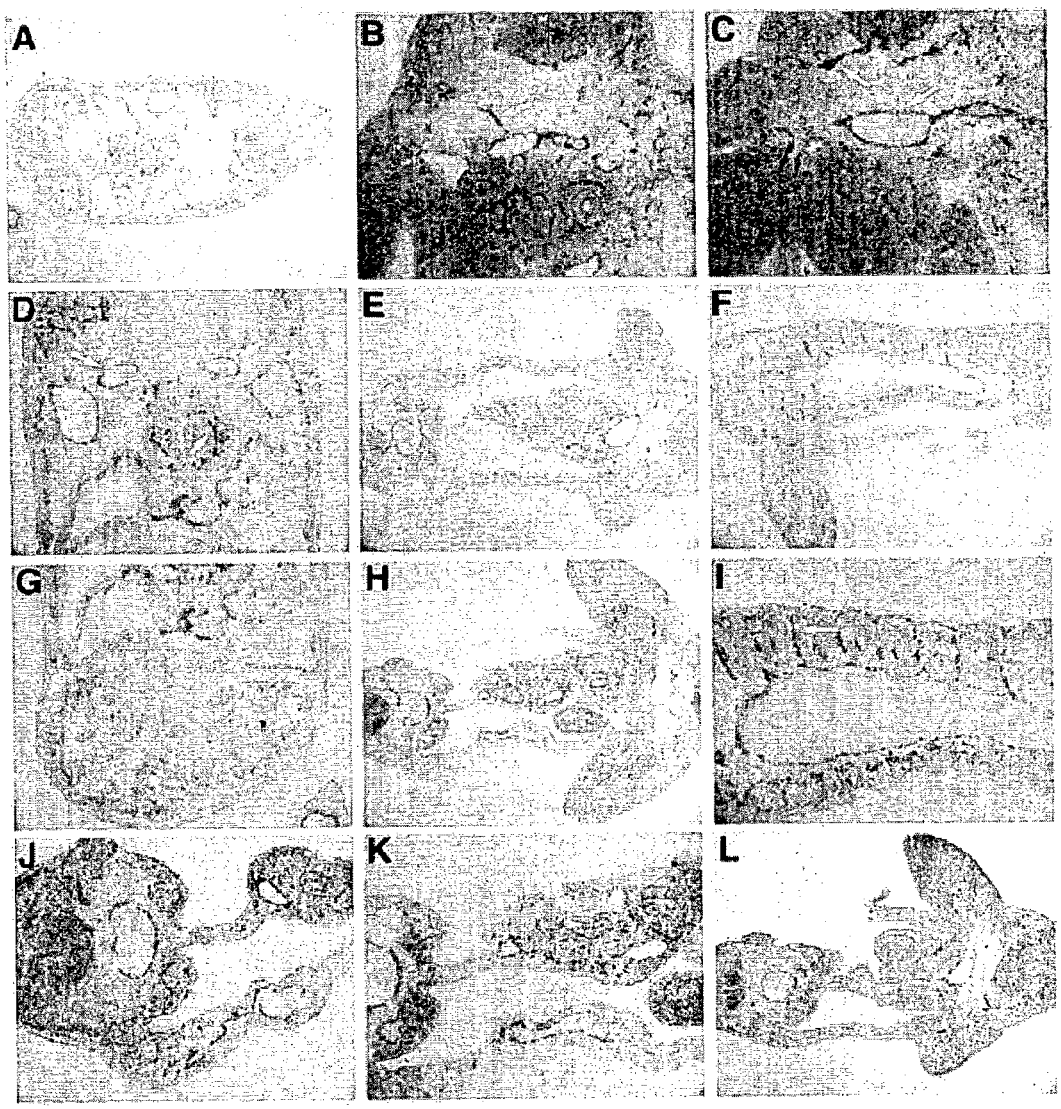
FIG. 2. In situ hybridization to sections of day 10.5 (E10.5) mouse embryos with a D1-1 cRNA probe. White arrows indicate the specific expression of D1-1 in the endothelium. Specific expression is not detected in any other tissues at this stage.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article, unless context clearly indicates otherwise. By way of example, "an element" means one element or more than one element.

The term "angiogenesis associated disease or process" as used herein refers to any disease or process that is either mediated by angiogenesis or associated with angiogenesis, including non-pathological conditions, such as blood vessel development during embryo implantation and the normal angiogenic processes in a healthy vertebrate.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

A "chimeric polypeptide" or "fusion polypeptide" is a fusion of a first amino acid sequence with a second amino acid sequence where the first and second amino acid sequences are not naturally present in a single polypeptide chain.

The term "D1-1 nucleic acid" includes nucleic acids comprising sequences that code for D1-1 polypeptides, including a nucleic acid comprising a sequence as represented in any of SEQ ID NOs: 1-3, 7-9, 13-15 and 19-21, and also including variants.

The term "D1-1 polypeptide" includes any polypeptide comprising a sequence as represented in any of SEQ ID NOs: 4-6, 10-12, 16-18 and 22-24, as well as any of the variants described herein. The term D1-1 polypeptide also includes any polypeptide comprising a conserved domain from a D1-1 polypeptide, such as a domain that is at least 85% identical to one or more of SEQ ID Nos. 6, 12, 18 or 24, and particularly Type I membrane proteins comprising a conserved 30 domain. The term "human D1-1 polypeptide" refers to any naturally occurring D1-1 polypeptide found in humans. The same applies to "bovine", "murine" or "porcine" D1-1 polypeptides. The term "non-human D1-1 polypeptide" includes any D1-1 polypeptides that are not found in humans. The term "variants" is used herein to include all fragments, mutants and derivatives of a nucleic acid or a polypeptide. For example, "variants" may include substitutions of naturally occurring amino acids at specific sites with other molecules, including but not limited to naturally and non-naturally occurring amino acids.

A "D1-1 associated protein" refers to a protein capable of interacting with and/or binding to a D1-1 polypeptide. Generally, the D1-1 associated protein may interact directly or indirectly with the D1-1 polypeptide.

The term "detection", in addition to art-recognized meanings, is intended to refer to any process of observing a marker, in a biological sample, whether or not the marker is actually detected. In other words, the act of probing a sample for a marker is a "detection" even if the marker is determined to be not present or below the level of sensitivity. Detection may be a quantitative, semi-quantitative or non-quantitative observation.

An "expression construct" is any recombinant nucleic acid that includes an expressible nucleic acid and regulatory elements sufficient to mediate expression in a suitable host cell. For example, an expression construct may contain a promoter or other RNA polymerase contact site, a transcription start site or a transcription termination sequence. An expression construct for production of a protein may contain, for example a translation start site, such as an ATG codon, a ribosome binding site, such as a Shine-Dalgamo sequence, or a translation stop codon.

The term "including" is used herein to mean, and is used interchangeably with, the phrase "including but not limited to".

The term "isolated" as used in reference to nucleic acids or polypeptides indicates a nucleic acid or polypeptide, such as a D1-1 nucleic acid or polypeptide, that is removed from its natural context. For example, an "isolated" polypeptide may be substantially free of other proteins that are normally associated with it. As another example, an "isolated" nucleic acid may be removed from its normal genomic context and recombined with other nucleic acids, such as a cloning vector.

A "knock-out" of a gene means an alteration in the sequence of the gene that results in a decrease of function of the target gene, preferably such that target gene expression is undetectable or insignificant. A knock-out of an endogenous D1-1 gene means that function of the endogenous D1-1 gene has been substantially decreased. "Knock-out" transgenics can be transgenic animals having a heterozygous knock-out of the D1-1 gene or a homozygous knock-out of the D1-1 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased) of the target gene, e.g., by introduction of an additional copy of the target gene, or by operatively inserting a regulatory sequence that provides for enhanced expression of an endogenous copy of the target gene. "Knock-in" transgenics of interest for the present invention can be transgenic animals having a knock-in of the animal's endogenous D1-1. Such transgenics can be heterozygous knock-in for the D1-1 gene, homozygous for the knock-in of the D1-1 gene. "Knock-ins" also encompass conditional knock-ins.

The term "nucleic acid" includes, in addition to any art recognized meaning, polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "or" is used herein to mean, and is used interchangeably with, the term "and/or", unless context clearly indicates otherwise.

The terms "polypeptide" and "protein" are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "recombinant" as used in reference to a nucleic acid indicates any nucleic acid that is positioned adjacent to one or more nucleic acid sequences that it is not found adjacent to in nature. A recombinant nucleic acid may be generated in vitro, for example by using the methods of molecular biology, or in vivo, for example by insertion of a nucleic acid at a novel chromosomal location by homologous or non-homologous recombination. The term "recombinant" as used in reference to a polypeptide indicates any polypeptide that is produced by expression and translation of a recombinant nucleic acid.

The term "transgene" is used herein to describe genetic material which has been or is about to be artificially inserted into the genome of a mammal, particularly a mammalian cell of a living animal.

By "transgenic animal" is meant a non-human animal, usually a mammal (e.g., mouse, rat, rabbit, hamster, etc.), having a non-endogenous nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

2. D1-1 Polypeptides

In certain aspects, the invention provides D1-1 polypeptides of various mammals and functional variants thereof. Preferred functional variants of D1-1 polypeptides are those that have angiogenesis modulating activity. By "angiogenesis modulating activity", it is meant to include both angiogenesis promoting activity and angiogenesis inhibitory activity. In certain aspects, the present invention includes the full-length D1-1 protein and variants of the D1-1 protein, which include biologically-active fragments of the D1-1 protein and fusion proteins including at least a portion of the D1-1 protein. These include proteins with D1-1 activity that have amino acid substitutions or have sugars or other molecules attached to amino acid functional groups.

In certain aspects, the present disclosure makes available isolated and/or purified forms of the D1-1 polypeptides, which are isolated from, or otherwise substantially free of, other proteins which might normally be associated with the protein or a particular complex including the protein. In certain embodiments, a D1-1 polypeptide is any polypeptide (particularly a non-human polypeptide) comprising a conserved D1-1 domain, such as a domain that is at least 85% identical to an amino acid sequence of SEQ ID NO: 6, 12, 18 or 24, and optionally the conserved domain is at least 90%, 95%, 98%, 99% or 100% identical to a sequence of SEQ ID NO: 6, 12, 18 or 24. In certain embodiments, a D1-1 polypeptide is a polypeptide that comprises an amino acid sequence that is at least 85%, 90%, 95%, 97%, 99% or 100% identical to the amino acid sequence of SEQ ID No: 4, 10, and 16. In certain embodiments, a D1-1 polypeptide is a polypeptide comprising a portion of an amino acid sequence that is at least 60%, 70%, 80%, 85%, 90%, 95%, 97%, 99% or 100% identical to any of SEQ ID Nos: 4, 5, 10, 11, 16, 17, 22 and 23, and preferably wherein said portion is a functional portion, such as a portion that is sufficient to modulate angiogenesis. In certain embodiments a D1-1 polypeptide is a polypeptide obtained when a nucleic acid comprising a nucleic acid sequence at least 85%, 90%, 95%, 97%, 99% or 100% identical to a nucleic acid sequence of SEQ ID NO: 1, 7, 13 or 20 is expressed in cell. In certain embodiments a D1-1 polypeptide is purified or partially purified.

Optionally, a D1-1 polypeptide of the invention will function in place of an endogenous D1-1 polypeptide, for example by mitigating a partial or complete D1-1 loss of function phenotype in a cell. For example, a D1-1 polypeptide of the invention may be produced in a cell in which endogenous D1-1 has been reduced, and the introduced D1-1 polypeptide will mitigate a phenotype resulting from the endogenous D1-1 reduction. An exemplary D1-1 loss of function phenotype is a change in angiogenesis activities in vivo.

In another aspect, the invention provides polypeptides that are agonists or antagonists of a D1-1 polypeptide. Variants of a D1-1 polypeptide may have a hyperactive or constitutive activity, or, alternatively, act to prevent D1-1 polypeptides from performing one or more functions. For example, a truncated form lacking one or more domain may have a dominant negative effect.

Another aspect of the invention relates to polypeptides derived from a full-length D1-1 polypeptide. Isolated peptidyl portions of the subject proteins can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, any one of the subject proteins can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a D1-1 polypeptide.

Full-length, naturally occurring D1-1 proteins are transmembrane proteins, with a portion of the protein that is positioned outside the cell (the extracellular portion) and a portion of the protein that is positioned inside the cell (the intracellular portion). Extracellular domains may comprise amino acids 1-131 of the SEQ ID NO:4, amino acids 1-126 of the SEQ ID NO:10, amino acids 1-160 of the SEQ ID NO:16, amino acids 1-110 of the SEQ ID NO:22. D1-1 polypeptides typically include a signal sequence that mediates extrusion of the extracellular domain from many cell types, for example, an extracellular portion of a D1-1 polypeptide, such as SEQ ID Nos. 5, 11, 17 and 23 may be expressed with an N-terminal signal peptide. In cells that recognize the signal sequence (e.g. most mammalian cells), the signal sequence will be cleaved off. One aspect of the invention includes polypeptides comprising an extracellular portion of the D1-1 protein. In a further aspect of the invention, these D1-1 variants comprising D1-1 extracellular domains have angiogenesis inhibitory activities. D1-1 extracellular portions that are smaller than those described above may also be employed, so long as the portion retains an activity, such as the ability to inhibit angiogenesis.

In certain embodiments, the present invention also includes D1-1 fragments comprising the transmembrane domain or the intracellular domain of the D1-1 protein. Transmembrane domains comprise amino acid 132-154 of the SEQ ID NO:4, amino acid 127-150 of the SEQ ID NO:10, amino acid 161-184 of the SEQ ID NO:16, amino acid 111-133 of the SEQ ID NO:22. Intracellular domain comprise amino acid 154-214 of the SEQ ID NO:4, amino acid 151-204 of the SEQ ID NO:10, amino acid 185-238 of the SEQ ID NO:16, amino acid 134-183 of the SEQ ID NO:22.

It is also possible to modify the structure of the subject D1-1 polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the D1-1 polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a D1-1 polypeptide can be assessed, e.g., for their ability to modulate angiogenesis, their ability to bind to another polypeptide, e.g., another D1-1 polypeptide or another protein involved in angiogenesis. Polypeptides in which more than one replacement has taken place can readily be tested in the same manner.

This invention further contemplates a method of generating sets of combinatorial mutants of the D1-1 polypeptides, as well as truncation mutants, and is especially useful for identifying potential variant sequences (e.g. homologs) that are functional in binding to a D1-1 polypeptide. The purpose of screening such combinatorial libraries may be to generate, for example, D1-1 homologs which can act as either agonists or antagonist, or alternatively, which possess novel activities all together. Combinatorially-derived homologs can be generated which have a selective potency relative to a naturally occurring D1-1 polypeptide. Such proteins, when expressed from recombinant DNA constructs, can be used in gene therapy protocols.

Likewise, mutagenesis can give rise to variants which have intracellular half-lives dramatically different than the corresponding wild-type protein. For example, the altered protein can be rendered either more stable or less stable to proteolytic degradation or other cellular process which result in destruction of, or otherwise inactivation of the D1-1 polypeptide of interest. Such variants, and the genes which encode them, can be utilized to alter D1-1 levels by modulating the half-life of the protein. For instance, a short half-life can give rise to more transient biological effects and, when part of an inducible expression system, can allow tighter control of recombinant D1-1 levels within the cell. As above, such proteins, and particularly their recombinant nucleic acid constructs, can be used in gene therapy protocols.

In similar fashion, D1-1 homologs can be generated by the present combinatorial approach to act as antagonists, in that they are able to interfere with the ability of the corresponding wild-type protein to function.

In a representative embodiment of this method, the amino acid sequences for a population of D1-1 homologs are aligned, preferably to promote the highest homology possible. Such a population of variants can include, for example, homologs from one or more species, or homologs from the same species but which differ due to mutation. Amino acids which appear at each position of the aligned sequences may be selected to create a degenerate set of combinatorial sequences. In a preferred embodiment, the combinatorial library is produced by way of a degenerate library of genes encoding a library of polypeptides which each include at least a portion of potential D1-1 sequences. For instance, a mixture of synthetic oligonucleotides can be enzymatically ligated into gene sequences such that the degenerate set of potential D1-1 nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential D1-1 sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382, as well as U.S. Pat. Nos. 5,223,409, 5,198,346, and 5,096,815).

Alternatively, other forms of mutagenesis can be utilized to generate a combinatorial library. For example, D1-1 variants (both agonist and antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193: 653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of D1-1 polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of D1-1 variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate combinatorial gene products of one of the subject proteins are displayed on the surface of a cell or virus, and the ability of particular cells or viral particles to bind a D1-1 polypeptide is detected in a "panning assay". For instance, a library of D1-1 variants can be cloned into the gene for a surface membrane protein of a bacterial cell (Ladner et al., WO 88/06630; Fuchs et al., (1991) Bio/Technology 9:1370-1371; and Goward et al., (1992) TIBS 18:136-140), and the resulting fusion protein detected by panning, e.g. using a fluorescently labeled molecule which binds the D1-1 polypeptide, to score for potentially functional homologs. Cells can be visually inspected and separated under a fluorescence microscope, or, where the morphology of the cell permits, separated by a fluorescence-activated cell sorter.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical $E.$ $coli$ filamentous phages M13, fd, and f1 are most often used in phage display libraries, as either of the phage gIII or gVIII coat proteins can be used to generate fusion proteins without disrupting the ultimate packaging of the viral particle (Ladner et al., PCT publication WO 90/02909; Garrard et al., PCT publication WO 92/09690; Marks et al., (1992) J. Biol. Chem. 267:16007-16010; Griffiths et al., (1993) EMBO J. 12:725-734; Clackson et al., (1991) Nature 352:624-628; and Barbas et al., (1992) PNAS USA 89:4457-4461).

In certain embodiments, the invention also provides for reduction of the subject D1-1 polypeptides to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a D1-1 polypeptide which participate in protein-protein interactions involved in, for example, binding of proteins involved in angiogenesis to each other. To illustrate, the critical residues of a D1-1 polypeptide which are involved in molecular recognition of a substrate protein can be determined and used to generate D1-1 polypeptide-derived peptidomimetics which bind to the substrate protein, and by inhibiting D1-1 binding, act to inhibit its biological activity. By employing, for example, scanning mutagenesis to map the amino acid residues of a D1-1 polypeptide which are involved in binding to another polypeptide, peptidomimetic compounds can be generated which mimic those residues involved in binding. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., (1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

D1-1 polypeptides may further comprise post-translational or non-amino acid elements, such as hydrophobic modifications (e.g. polyethylene glycols or lipids), poly- or monosaccharide modifications, phosphates, acetylations, etc. Effects of such elements on the functionality of a D1-1 polypeptide may be tested as described herein for other D1-1 variants.

In certain embodiments, invention also provides fusion proteins comprising D1-1 protein and a heterologous protein. In certain embodiments, the fusion proteins comprise at least a portion of the D1-1 or a variant thereof and a second domain selected from the group consisting of an immunoglobulin element, a multimerizing domain, a targeting domain, a stabilizing domain, and a purification domain. Any one domain may perform many functions. For example, an Fc domain may provide dimerization, facilitate purification and stabilize the protein in vivo. Exemplary heterologous proteins that can be used to generate D1-1 fusion proteins include, but are not limited to, glutathione-S-transferase (GST), an enzymatic activity such as alkaline phosphatase (AP), or an epitope tag such as hemaglutinin (HA).

An immunoglobulin element may be any portion of an immunoglobulin. In certain embodiments, the immunoglobulin element comprises one or more domains of an IgG heavy chain. For example, an immunoglobulin element may comprise a heavy chain or a portion thereof from an IgG, IgD, IgA or IgM. Immunoglobulin heavy chain constant region domains include CH1, CH2, CH3, and CH4 of any class of immunoglobulin heavy chain including gamma, alpha, epsilon, mu, and delta classes. Immunoglobulin variable regions include VH, Vkappa, or Vgamma. An Fc portion is a commonly used immunoglobulin element.

In certain embodiments, a D1-1 is fused to a multimerization domain, such as a dimerization domain. Multimerization domains may be essentially any polypeptide that forms a dimer (or higher order complex, such as a trimer, tetramer, etc.) with another polypeptide. Optionally, the multimerization polypeptide associates with other, identical multimerization polypeptides, thereby forming homomultimers. An IgG Fc element is an example of a dimerizing domain that tends to form homomultimers. Optionally, the multimerizing polypeptide associates with other different multimerizing polypeptides, thereby forming heteromultimers. The Jun leucine zipper domain forms a dimer with the Fos leucine zipper domain, and is therefore an example of a dimerizing domain that tends to form heteromultimers. Multimerizing domains may form both hetero- and homomultimers.

Different elements of fusion proteins may be arranged in any manner that is consistent with the desired functionality. For example, a D1-1 may be placed C-terminal to a heterologous domain, or, alternatively, a heterologous domain may be placed C-terminal to a D1-1. The D1-1 and the heterologous domain need not be adjacent in a fusion protein, and additional domains or amino acid sequences may be included C- or N-terminal to either domain or between the domains.

The disclosure further provides methods for testing the functionality of D1-1 polypeptides, variants and fragments using angiogenesis assays, including CAM assay, mouse corneal assay and others.

3. D1-1 Nucleic Acids and Expression Vectors

In certain aspects the invention provides isolated and/or recombinant nucleic acids encoding D1-1 polypeptides, such as, for example, SEQ ID Nos: 1-3, 7-9, 13-16 and 22-24. Nucleic acids of the invention are further understood to include nucleic acids that comprise variants of SEQ ID Nos: 1-3, 7-9, 13-16 and 22-24. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID Nos: 1-3, 7-9, 13-16 and 22-24, e.g. due to the degeneracy of the genetic code. For example, nucleic acids encoding D1-1 polypeptides may be nucleic acids comprising a sequence that is at least 85%, 90%, 95%, 99% or 10% identical to a sequence of SEQ ID Nos: 1-3, 7-9, 13-16 and 22-24 or a sequence that encodes a polypeptide of SEQ ID Nos: 4-6, 10-12, 16-18 and 22-24. In other embodiments, variants will also include sequences that will hybridize under highly stringent conditions to a coding sequence of a nucleic acid sequence designated in SEQ ID Nos: 1-3, 7-9, 13-16 and 22-24.

One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50 ° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from SEQ ID Nos: 1-3, 7-9, 13-16 and 22-24 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. One skilled in the art will appreciate that these variations in one or more nucleotides of the nucleic acids encoding a particular protein may exist among individuals of a given species due to natural allelic variation. Any and all such nucleotide variations and resulting amino acid polymorphisms are within the scope of this invention.

Optionally, a D1-1 nucleic acid of the invention will genetically complement a partial or complete D1-1 loss of function phenotype. For example, a D1-1 nucleic acid of the invention may be expressed in a cell in which endogenous D1-1 has been knocked out, and the introduced D1-1 nucleic acid will mitigate a phenotype resulting from the knockout.

In certain aspects, nucleic acids encoding D1-1 polypeptides and variants thereof may be used to increase D1-1 expression in an organism or cell by direct delivery of the nucleic acid. A nucleic acid therapy construct of the present invention can be delivered, for example, as an expression plasmid which, when transcribed in the cell, produces RNA which encodes a D1-1 polypeptide.

In another aspect, nucleic acid encoding D1-1 polypeptides and variants thereof may be used to decrease D1-1 expression. Such a nucleic acid therapy construct can be delivered, for example, as an expression plasmid which, when transcribed in the cell, produces RNA which is complementary to at least a unique portion of the cellular mRNA which encodes a D1-1 polypeptide. Alternatively, the construct is an oligonucleotide which is generated ex vivo and which, when introduced into the cell causes inhibition of expression by hybridizing with the mRNA and/or genomic sequences encoding a D1-1 polypeptide. Such oligonucleotide probes are optionally modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) *Biotechniques* 6:958-976; and Stein et al., (1988) *Cancer Res* 48:2659-2668.

Another aspect of the invention relates to the use of RNA interference (RNAi) to effect knockdown of D1-1 genes. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Ribozyme molecules designed to catalytically cleave an mRNA transcripts can also be used to prevent translation of MRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells that in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

A further aspect of the invention relates to the use of DNA enzymes to inhibit expression of D1-1 gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

Briefly, to design an ideal DNA enzyme that specifically recognizes and cleaves a target nucleic acid, one of skill in the art must first identify the unique target sequence. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No 6,110,462. Additionally, one of skill in the art will recognize that, like antisense oligonucleotide, DNA enzymes can be optionally modified to improve stability and improve resistance to degradation.

Accordingly, the modified oligomers of the invention are useful in therapeutic, diagnostic, and research contexts. In therapeutic applications, the oligomers are utilized in a manner appropriate for nucleic acid therapy in general.

In addition to use in therapy, the oligomers of the invention may be used as diagnostic reagents to detect the presence or absence of the D1-1 DNA or RNA sequences to which they specifically bind, such as for determining the level of expression of a gene of the invention or for determining whether a gene of the invention contains a genetic lesion.

In another aspect of the invention, the subject nucleic acid is provided in an expression vector comprising a nucleotide sequence encoding a subject D1-1 polypeptide and operably linked to at least one regulatory sequence. Regulatory sequences are art-recognized and are selected to direct expression of the D1-1 polypeptide. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a D1-1 polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As will be apparent, the subject gene constructs can be used to cause expression of the subject D1-1 polypeptides in cells propagated in culture, e.g. to produce proteins or polypeptides, including fusion proteins or polypeptides, for purification.

This invention also pertains to a host cell transfected with a recombinant gene including a coding sequence for one or more of the subject D1-1 polypeptides. The host cell may be any prokaryotic or eukaryotic cell. For example, a polypeptide of the present invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject D1-1 polypeptides. For example, a host cell transfected with an expression vector encoding a D1-1 polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically or in a membrane fraction and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the D1-1 polypeptide is a fusion protein containing a domain which facilitates its purification, such as a D1-1-GST fusion protein, D1-1-intein fusion protein, D1-1-cellulose binding domain fusion protein, D1-1-polyhistidine fusion protein etc.

A nucleotide sequence encoding a D1-1 polypeptide can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures.

A recombinant D1-1 nucleic acid can be produced by ligating the cloned gene, or a portion thereof, into a vector suitable for expression in either prokaryotic cells, eukaryotic cells, or both. Expression vehicles for production of a recombinant D1-1 polypeptides include plasmids and other vectors. For instance, suitable vectors for the expression of a D1-1 polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant D1-1 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

It is well known in the art that a methionine at the N-terminal position can be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS* USA 84:2718-1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable, e.g., to produce an immunogenic fragment of a D1-1 polypeptide. For example, the VP6 capsid protein of rotavirus can be used as an immunologic carrier protein for portions of polypeptide, either in the monomeric form or in the form of a viral particle. The nucleic acid sequences corresponding to the portion of the D1-1 polypeptide to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a D1-1 polypeptide and the poliovirus capsid protein can be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

The Multiple Antigen Peptide system for peptide-based immunization can be utilized, wherein a desired portion of a D1-1 polypeptide is obtained directly from organo-chemical synthesis of the peptide onto an oligomeric branching lysine core (see, for example, Posnett et al., (1988) *JBC* 263:1719 and Nardelli et al., (1992) *J. Immunol.* 148:914). Antigenic determinants of a D1-1 polypeptide can also be expressed and presented by bacterial cells.

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified D1-1 polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Truncated Extracellular D1-1 Polypeptides

Certain naturally occurring D1-1 proteins disclosed herein are transmembrane proteins, with a portion of the protein positioned outside the cell (the extracellular portion) and a portion of the protein positioned inside the cell (the intracellular portion). Aspects of the present invention encompass polypeptides comprising truncated portions of D1-1 polypeptides, including extracellular, intracellular or transmembrane portions.

In certain embodiments, the invention provides "truncated extracellular D1-1 polypeptides". The term "truncated extracellular D1-1 polypeptide" is intended to refer to a polypeptide consisting of or comprising an amino acid sequence of an extracellular domain of a naturally occurring D1-1 polypeptide, either including or excluding any signal sequence and sequence N-terminal to the signal sequence, or an amino acid sequence that is at least 33 percent identical to an extracellular domain of a naturally occurring D1-1 polypeptide, and optionally at least 60%, 70%, 80%, 85%, 90%, 95%, 98%, 99% or 100% identical to the sequence of an extracellular domain of a naturally occurring D1-1 polypeptide, as exemplified by SEQ ID Nos. 5, 11, 17 and 23. The term "truncated extracellular D1-1 polypeptide" accordingly encompasses isolated extracellular portions of D1-1 polypeptides, variants thereof, fragments thereof and fusion proteins comprising any of the preceding. The term "truncated extracellular D1-1 polypeptide" is explicitly intended to exclude any full-length, naturally occurring D1-1 polypeptide. In certain embodiments, a truncated extracellular D1-1 polypeptide will be devoid of any transmembrane domain, and may be referred to as a "soluble D1-1 polypeptide". In certain embodiments, a truncated extracellular D1-1 polypeptide may include a naturally associated or engineered membrane domain.

In certain embodiments, truncated extracellular D1-1 polypeptides comprise an extracellular portion of a naturally occurring D1-1 protein such as a sequence of any of SEQ ID Nos: 5, 11, 17 and 23. In certain embodiments, a truncated extracellular D1-1 polypeptide comprises an amino acid sequence that is at least 60%, 70%, 80%, 85%, 90%, 95%, 98% or 99% identical to an amino acid sequence of any of SEQ ID Nos: 5, 11, 17 and 23. In certain embodiments, a truncated extracellular D1-1 polypeptide comprises at least 30, 40 or 50 consecutive amino acids of an amino acid sequence of any of SEQ ID Nos: 5, 11, 17 and 23. Optionally, the truncated extracellular D1-1 polypeptide comprises the endogenous signal sequence, such as a sequence comprising amino acids 1-131 of the SEQ ID NO:4, amino acids 1-126 of the SEQ ID NO:10, amino acids 1-160 of the SEQ ID NO:16, or amino acids 1-110 of the SEQ ID NO:22. In one aspect of the invention, truncated extracellular D1-1 polypeptides comprising the extracellular domains of D1-1 have angiogenesis inhibitory activities. In addition, aspects of the invention also include variants of truncated extracellular D1-1 polypeptides.

Truncated extracellular D1-1 polypeptides may be produced by removing the cytoplasmic tail and the transmembrane region. Alternatively, the transmembrane domain may be inactivated by deletion, or by substitution of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes.

Truncated extracellular D1-1 polypeptides may additionally include any number of well-known leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native D1-1 signal sequence may be used to effect extrusion from the cell.

The invention further encompasses fusion proteins comprising a truncated extracellular D1-1 polypeptide and a heterologous protein. In certain embodiments, fusion proteins comprising truncated extracellular D1-1 polypeptide and an immunoglobulin element are provided. An exemplary immunoglobulin element is a constant region like the Fc domain of a human IgG1 heavy chain (Browning et al., J. Immunol., 154, pp. 33-46 (1995)). Soluble receptor-IgG fusion proteins are common immunological reagents and methods for their construction are known in the art (see e.g., U.S. Pat. No. 5,225,538). In a further embodiment, the fusion proteins comprise a truncated extracellular D1-1 polypeptide and a second heterologous polypeptide to increase the in vivo stability of the fusion protein, or to modulate its biological activity or localization, or to facilitate purification of the fusion protein. Other exemplary heterologous proteins that can be used to generate D1-1 soluble fusion proteins include, but not limited to, glutathione-S-transferase (GST), an enzymatic activity such as alkaline phosphatase (AP), or an epitope tag such as hemaglutinin (HA). The truncated extracellular D1-1 fusion proteins may be constructed as outlined in Section 2 for D1-1 polypeptide.

Optionally, stable plasma proteins—which typically have a half-life greater than 20 hours in the circulation—are used to construct the receptor fusion proteins. Such plasma proteins include but are not limited to: immunoglobulins, serum albumin, lipoproteins, apolipoproteins and transferrin. Sequences that can target the truncated extracellular D1-1 molecule to a particular cell or tissue type may also be attached to the truncated extracellular D1-1 to create a specifically-localized truncated extracellular D1-1 protein that is a fusion protein.

An exemplary truncated extracellular D1-1 protein is a D1-1 extracellular portion fused to the Fc portion of the mouse immunoglobulin, set forth in SEQ ID NO: 26 and encoded by the sequence of SEQ ID NO:25. An exemplary human D1-1:Fc fusion is set forth in SEQ ID NO: 28 and encoded by SEQ ID NO: 27.

In certain embodiments, the invention includes nucleic acids encoding truncated extracellular D1-1 polypeptides comprising the extracellular portions of the D1-1 proteins. In further embodiments, this invention also pertains to a host cell comprising truncated extracellular D1-1 polypeptides and related derivatives. The host cell may be any prokaryotic or eukaryotic cell. For example, a polypeptide of the present invention may be expressed in bacterial cells such as E. coli, insect cells (e.g., using a baculovirus expression system), yeast, or mammalian cells. Other suitable host cells are known to those skilled in the art. Accordingly, some embodiments of the present invention further pertain to methods of producing the truncated extracellular D1-1 polypeptides, using methods described in Section 2 for D1-1 polypeptides.

5. Antibodies

Another aspect of the invention pertains to an antibody reactive with a D1-1 polypeptide, preferably antibodies that are specifically reactive with D1-1 polypeptide. For example, by using immunogens derived from a D1-1 polypeptide, anti-protein/anti-peptide antisera or monoclonal antibodies can be made by standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a D1-1 polypeptide or an antigenic fragment which is capable of eliciting an antibody response, or a fusion protein). Techniques for conferring immunogenicity on a protein or peptide include conjugation to carriers or other techniques well known in the art. An immunogenic portion of a D1-1 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a D1-1 polypeptide of a mammal, e.g., antigenic determinants of a protein set forth in SEQ ID Nos: 4-6, 10-12, 16-18 and 22-24.

In one embodiment, antibodies are specific for the D1-1 proteins as encoded by nucleic acid sequences as set forth in any of SEQ ID Nos: 1-3, 7-9, 13-15 and 19-21.

In one embodiment, antibodies of the invention are specific for the extracellular portion of the D1-1 protein, such as a sequence at least 60%, 70%, 80%, 85%, 90%, 95%, 98%, 99% or 100% identical to a sequence of any of SEQ ID Nos: 5, 11, 17 and 23. In a set of exemplary embodiments, an antibody binds to an extracellular portion represented by amino acids 1-131 of the SEQ ID NO:4, amino acids 1-126 of the SEQ ID NO:10, amino acids 1-160 of the SEQ ID NO:16, or amino acids 1-110 of the SEQ ID NO:24. In another embodiment, antibodies of the invention are specific for the intracellular portion or the transmembrane portion of the D1-1 protein. In a further embodiment, antibodies of the invention are specific for the truncated extracellular D1-1 proteins and variants thereof, as described above in Section 4.

Following immunization of an animal with an antigenic preparation of a D1-1 polypeptide, anti-D1-1 antisera can be obtained and, if desired, polyclonal anti-D1-1 antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian D1-1 polypeptide of the present invention and monoclonal antibodies isolated from a culture comprising such hybridoma cells.

The term antibody as used herein is intended to include fragments thereof which are also specifically reactive with one of the subject D1-1 polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a D1-1 polypeptide conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

In certain preferred embodiments, an antibody of the invention is a monoclonal antibody, and in certain embodiments the invention makes available methods for generating novel antibodies. For example, a method for generating a monoclonal antibody that binds specifically to a D1-1 polypeptide may comprise administering to a mouse an amount of an immunogenic composition comprising the D1-1 polypeptide effective to stimulate a detectable immune response, obtaining antibody-producing cells (e.g. cells from the spleen) from the mouse and fusing the antibody producing cells with myeloma cells to obtain antibody-producing hybridomas, and testing the antibody-producing hybridomas to identify a hybridoma that produces a monocolonal antibody that binds specifically to the D1-1 polypeptide. Once obtained, a hybridoma can be propagated in a cell culture, optionally in culture conditions where the hybridoma-derived cells produce the monoclonal antibody that binds specifically to the D1-1 polypeptide. The monoclonal antibody may be purified from the cell culture.

Anti-D1-1 antibodies can be used, e.g., to detect D1-1 polypeptides in biological samples and/or to monitor D1-1 polypeptide levels in an individual, for determining whether or not said individual is inflicted with an angiogenesis associated disease, or providing prognosis for such individuals inflicted with angiogenesis associated disease, or allowing determination of the efficacy of a given treatment regimen for such individuals. The level of D1-1 polypeptide may be measured in a variety of sample types such as, for example, in cells, stools, and/or in bodily fluid, such as in whole blood samples, blood serum, blood plasma and urine. The adjective "specifically reactive with" as used in reference to an antibody is intended to mean, as is generally understood in the art, that the antibody is sufficiently selective between the antigen of interest (e.g. a D1-1 polypeptide) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that is effective at selectively identifying an antigen of interest in one type of biological sample (e.g. a stool sample) may not be as effective for selectively identifying the same antigen in a different type of biological sample (e.g. a blood sample). Likewise, an antibody that is effective at identifying an antigen of interest in a purified protein preparation that is devoid of other biological contaminants may not be as effective at identifying an antigen of interest in a crude biological sample, such as a blood or urine sample. Accordingly, in preferred embodiments, the application provides antibodies that have demonstrated specificity for an antigen of interest in a sample type that is likely to be the sample type of choice for use of the antibody. In a particularly preferred embodiment, the application provides antibodies that bind specifically to a D1-1 polypeptide in a protein preparation from blood (optionally serum or plasma) from a patient that has a colon neoplasia or that bind specifically in a crude blood sample (optionally a crude serum or plasma sample).

One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g. by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

Another application of anti-D1-1 antibodies of the present invention is in the immunological screening of cDNA libraries constructed in expression vectors such as gt11, gt18-23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a D1-1 polypeptide, e.g., other orthologs of a particular protein or other paralogs from the same species, can then be detected with antibodies, as, for example, reacting nitrocellulose filters lifted from infected plates with the appropriate anti-D1-1 antibodies. Positive phage detected by this assay can then be isolated from the infected plate. Thus, the presence of D1-1 homologs can be detected and cloned from other animals, as can alternate isoforms (including splice variants) from humans.

6. Transgenic Animals

Another aspect of the invention features transgenic non-human animals which express a heterologous D1-1 gene, preferentially a human D1-1 gene. In another aspect the invention features transgenic non-human animals which have had one or both copies of the endogenous D1-1 genes disrupted in at least one of the tissue or cell-types of the animal. In one embodiment, the transgenic non-human animals is a mammal such as a mouse, rat, rabbit, goat, sheep, dog, cat, cow, or non-human primate. In certain embodiments, such a transgenic animal may display a phenotype associated with inadequate or excessive angiogenesis, and may therefore serve as a useful animal model to study the progression of diseases caused by such inadequate or excessive angiogenesis.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc. Preferably, the transgenic-animals are mice.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In one aspect of the invention, a D1-1 transgene can encode the wild-type form of the protein, homologs thereof, as well as antisense constructs. A D1-1 transgene can also encode a soluble form of D1-1 that has angiogenesis inhibitory activity.

It may be desirable to express the heterologous D1-1 transgene conditionally such that either the timing or the level of D1-1 gene expression can be regulated. Such conditional expression can be provided using prokaryotic promoter sequences which require prokaryotic proteins to be simultaneous expressed in order to facilitate expression of the D1-1 transgene. Exemplary promoters and the corresponding trans-activating prokaryotic proteins are given in U.S. Pat. No. 4,833,080.

Moreover, transgenic animals exhibiting tissue specific expression can be generated, for example, by inserting a tissue specific regulatory element, such as an enhancer, into the transgene. For example, the endogenous D1-1 gene promoter or a portion thereof can be replaced with another promoter and/or enhancer, e.g., a CMV or a Moloney murine leukemia virus (MLV) promoter and/or enhancer.

Transgenic animals containing an inducible D1-1 transgene can be generated using inducible regulatory elements (e.g. metallothionein promoter), which are well-known in the art. D1-1 transgene expression can then be initiated in these animals by administering to the animal a compound which induces gene expression (e.g. heavy metals). Another preferred inducible system comprises a tetracycline-inducible transcriptional activator (U.S. Pat. No. 5,654,168 issued Aug. 5, 1997 to Bujard and Gossen and U.S. Pat. No. 5,650,298 issued Jul. 22, 1997 to Bujard et al.).

The present invention provides for transgenic animals that carry the transgene in all their cells, as well as animals that carry the transgene in some, but not all cells, i.e., mosaic animals. The transgene can be integrated as a single transgene or in tandem, e.g., head to head tandems, or head to tail or tail to tail or as multiple copies.

The successful expression of the transgene can be detected by any of several means well known to those skilled in the art. Non-limiting examples include Northern blot, in situ hybridization of mRNA analysis, Western blot analysis, immunohistochemistry, and FACS analysis of protein expression.

In a further aspect, the invention features non-human animal cells containing a D1-1 transgene, preferentially a human D1-1 transgene. For example, the animal cell (e.g. somatic cell or germ cell (i.e. egg or sperm)) can be obtained from the transgenic animal. Transgenic somatic cells or cell lines can be used, for example, in drug screening assays. Transgenic germ cells, on the other hand, can be used in generating transgenic progeny, as described below.

Although not necessary to the operability of the invention, the transgenic animals described herein may comprise alterations to endogenous genes in addition to, or alternatively, to the genetic alterations described above. For example, the host animals may be either "knockouts" and/or "knockins" for a target gene(s) as is consistent with the goals of the invention (e.g., the host animal's endogenous D1-1 may be "knocked out"). Knockouts have a partial or complete loss of function in one or both alleles of an endogenous gene of interest. Knock-ins have an introduced transgene with altered genetic sequence and/or function from the endogenous gene. The two may be combined, for example, such that the naturally occurring gene is disabled, and an altered form introduced. For example, it may be desirable to knockout the host animal's endogenous D1-1 gene, while introducing an exogenous D1-1 gene (e.g., a human D1-1 gene).

In a knockout, preferably the target gene expression is undetectable or insignificant. For example, a knock-out of a D1-1 gene means that function of the D1-1 has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of APP genes. A functional knock-out may also be achieved by the introduction of an anti-sense construct that blocks expression of the native genes (for example, see Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser. The use of knockin technology may be combined with production of exogenous sequences to produce the transgenic animals of the invention.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

In certain embodiments, the invention further provides methods for identifying (screening) or for determining the safety and/or efficacy of therapeutics, i.e. compounds which are useful for treating and/or preventing the development of angiogenesis associated diseases. In addition, the assays are useful for further improving known therapeutic compounds, e.g, by modifying their structure to increase their stability and/or activity and/or toxicity.

The transgenic animals of the present invention may display angiogenesis related phenotypes, such as inadequate angiogenesis or excessive angiogenesis, depending on different alleles generated. For example, transgenic animals expressing a truncated extracellular D1-1 with angiogenesis inhibitory activity may have inadequate angiogenesis. As a result, the transgenic animals may have slow wound healing, inadequate vascularization of the uterine endometrium and associated infertility and other related symptoms. Accordingly, such transgenic animals can be used in in vivo assays to identify angiogenic therapeutics.

In an exemplary embodiment, the assay comprises administering a test compound to a transgenic animal of the invention, and comparing a phenotypic change in angiogenesis in the animal relative to a transgenic animal which has not received the test compound.

7. Screening Assays

Identification of role of D1-1 in angiogenesis allows for designing and screening for new angiogenesis modulating agents. In one aspect, the isolation of D1-1 facilitates rational design of D1-1 agonists and antagonists based on the structural features of D1-1 protein, which can be determined using X-ray crystallography, neuron diffraction, nuclear magnetic resonance spectrometry, and other techniques.

In addition, the present invention provides assays for identifying therapeutic agents that modulate angiogenesis. In certain embodiments, the therapeutic agents either interfere with or promote D1-1 function. In other embodiments, the therapeutic agents interfere with the interaction between D1-1 and a D1-1 associated polypeptide. In another embodiment, the therapeutic agents alter the expression level of endogenous D1-1 expression, by either increasing or decreasing D1-1 expression. In a further embodiment, the present invention provides assays for identifying therapeutic agents which either interfere with or promote the angiogenesis inhibitory activity of a truncated extracellular D1-1 polypeptide. In another embodiment, the assay detects agents which modulate the intrinsic biological activity of a D1-1 polypeptide or D1-1 complex, such as its angiogenesis modulating activity, binding to other cellular components, cellular compartmentalization, and the like.

Certain embodiments of the invention relate to assays for identifying agents that bind to a D1-1 polypeptide. Given that the D1-1 proteins are type I transmembrane proteins, agents that bind to D1-1 proteins may include their natural ligands, downstream signaling molecules, other endogenous polypeptides as well as artificial compounds. In one embodiment, an assay detects agents which inhibit interaction of one or more subject D1-1 polypeptides with a D1-1 associated protein. A wide variety of assays may be used for this purpose, including labeled in vitro protein-protein binding assays, electrophoretic mobility shift assays, interaction trap assay, immunoassays for protein binding, and the like.

Given the role of D1-1 in modulating angiogenesis, the agents that bind to D1-1 as well as the agents that interfere with D1-1 binding to D1-1 associated proteins may be able to modulate angiogenesis. Accordingly, one aspect of the invention provides a method for assessing the ability of an agent to modulate angiogenesis, comprising: 1) combining: a first polypeptide including at least a portion of a D1-1 polypeptide, a second polypeptide including at least a portion of a D1-1 associated protein that interacts with the first polypeptide, and an agent, under conditions wherein the first polypeptide interacts with the second polypeptide in the absence of said agent, 2) determining if said agent interferes with the interaction, and 3) for an agent that interferes with the interaction, further assessing its ability to interfere with D1-1 angiogenesis modulating activity in an angiogenesis assay.

Other embodiments of the invention include methods for assessing the ability of an agent to modulate angiogenesis comprising 1) combining a polypeptide including at least a portion of D1-1 and an agent under a condition wherein the D1-1 polypeptide modulate angiogenesis in an angiogenesis assay in the absence of the agent, and 2) determining if the agent interferes with or promotes the D1-1 modulation of angiogenesis.

Bioassays for angiogenesis inhibitory activity include the chick chorioallantoic membrane (CAM) assay, the mouse corneal assay, and assay for effect of administering isolated or synthesized proteins on implanted tumors. The CAM assay is described by O'Reilly, et al. in "Angiogenic Regulation of Metastatic Growth" Cell, vol. 79 (2), Oct. 1, 1994, pp. 315-328. Briefly, 3 day old chicken embryos with intact yolks are separated from the egg and placed in a petri dish. After 3 days of incubation, a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

A variety of assay formats will suffice and, in light of the present disclosure, those not expressly described herein will nevertheless be comprehended by one of ordinary skill in the art. Assay formats which approximate such conditions as formation of protein complexes, enzymatic activity, may be generated in many different forms, and include assays based on cell-free systems, e.g. purified proteins or cell lysates, as well as cell-based assays which utilize intact cells. Simple binding assays can also be used to detect agents which bind to D1-1. Such binding assays may also identify agents that act by disrupting the interaction between a D1-1 polypeptide and a D1-1 interacting protein. Agents to be tested can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide or oligonucleotide, having a molecular weight of less than about 2,000 daltons.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In preferred in vitro embodiments of the present assay, a reconstituted D1-1 complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in D1-1 complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure D1-1 complex assembly and/or disassembly.

Assaying D1-1 complexes, in the presence and absence of a candidate agent, can be accomplished in any vessel suitable for containing the reactants. Examples include microtitre plates, test tubes, and micro-centrifuge tubes. In a screening assay, the effect of a test agent may be assessed by, for example, assessing the effect of the test agent on kinetics, steady-state and/or endpoint of the reaction.

In one embodiment of the present invention, drug screening assays can be generated which detect inhibitory agents on the basis of their ability to interfere with assembly or stability of the D1-1 complex. In an exemplary binding assay, the compound of interest is contacted with a mixture comprising a D1-1 polypeptide and at least one interacting polypeptide. Detection and quantification of D1-1 complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation between the D1-1 polypeptides and a substrate polypeptide may be detected by a variety of techniques. For instance, modulation in the formation of complexes can be quantitated using, for example, detectably labeled proteins (e.g. radiolabeled, fluorescently labeled, or enzymatically labeled), by immunoassay, or by chromatographic detection. Surface plasmon resonance systems, such as those available from Biacore International AB (Uppsala, Sweden), may also be used to detect protein-protein interaction Often, it will be desirable to immobilize one of the polypeptides to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST-D1-1 fusion proteins can be adsorbed onto glutathione sepharose beads (Sigma Chemical, St. Louis, Mo.) or glutathione derivatized microtitre plates, which are then combined with a potential interacting protein, e.g. an 35S-labeled polypeptide, and the test compound and incubated under conditions conducive to complex formation . Following incubation, the beads are washed to remove any unbound interacting protein, and the matrix bead-bound radiolabel determined directly (e.g. beads placed in scintillant), or in the supernatant after the complexes are dissociated, e.g. when microtitre plate is used. Alternatively, after washing away unbound protein, the complexes can be dissociated from the matrix, separated by SDS-PAGE gel, and the level of interacting polypeptide found in the matrix-bound fraction quantitated from the gel using standard electrophoretic techniques.

In a further embodiment, agents that bind to a D1-1 may be identified by using an immobilized D1-1 (e.g. a D1-1 bound to a substrate). In an illustrative embodiment, a fusion protein can be provided which adds a domain that permits the protein to be bound to an insoluble matrix. For example, GST-D1-1 fusion proteins can be adsorbed onto glutathione sepharose beads (Sigma Chemical, St. Louis, Mo.) or glutathione derivatized microtitre plates, which are then combined with a potential labeled binding agent and incubated under conditions conducive to binding. Following incubation, the beads are washed to remove any unbound agent, and the matrix bead-bound label determined directly, or in the supernatant after the bound agent is dissociated. A D1-1:Fc fusion may be immobilized by binding to an Fc-affinity column, such as a protein A column.

In yet another embodiment, the D1-1 polypeptide and potential interacting polypeptide can be used to generate an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696), for subsequently detecting agents which disrupt binding of the proteins to one and other.

One aspect of the present invention provides reconstituted protein preparations including a D1-1 polypeptide and one or more interacting polypeptides.

In still further embodiments of the present assay, the D1-1 complex is generated in whole cells, taking advantage of cell culture techniques to support the subject assay. For example, as described below, the D1-1 complex can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high throughput analysis of candidate agents.

The components of the D1-1 complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In many embodiments, a cell is manipulated after incubation with a candidate agent and assayed for a D1-1 activity. In certain embodiments a D1-1 activity is represented by angiogenesis modulating activity. In certain embodiments, D1-1 activities may also include, without limitation, complex formation between D1-1 and its associated proteins. D1-1 complex formation may be assessed by immunoprecipitation and analysis of co-immunoprecipiated proteins or affinity purification and analysis of co-purified proteins. Fluorescence Resonance Energy Transfer (FRET)-based assays may also be used to determine complex formation. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (U.S. Pat. No. 5,981,200).

In a further embodiment, transcript levels may be measured in cells having higher or lower levels of D1-1 activity in order to identify genes that are regulated by D1-1. Promoter regions for such genes (or larger portions of such genes) may be operatively linked to a reporter gene and used in a reporter gene-based assay to detect agents that enhance or diminish D1-1-regulated gene expression. Transcript levels may be determined in any way known in the art, such as, for example, Northern blotting, RT-PCR, microarray, etc. Increased D1-1 activity may be achieved, for example, by introducing a strong D1-1 expression vector. Decreased D1-1 activity may be achieved, for example, by RNAi, antisense, ribozyme, gene knockout, etc.

In general, where the screening assay is a binding assay (whether protein-protein binding, agent-protein binding, etc.), one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° and 40° C. Incubation periods are selected for optimum activity, but may also be optimized to facilitate rapid high-throughput screening.

It is to be understood that the screening assays discussed above are applicable to identify therapeutic agents related to truncated extracellular D1-1 polypeptides and derivatives thereof. An exemplary derivative of truncated extracellular D1-1 polypeptides is a fusion protein containing truncated extracellular D1-1 polypeptide. Given the role of truncated extracellular D1-1 polypeptides in angiogenesis, compositions that perturb the formation or stability of the protein-protein interactions between truncated extracellular D1-1 polypeptides and the proteins that they interact with, such as D1-1-APs, are candidate pharmaceuticals for the treatment of angiogenesis associated diseases.

8. Methods and Compositions for Modulating Angiogenesis

Generally, there are two types of angiogenesis associated diseases: those involve excess angiogenesis and those involve inadequate angiogenesis. Thus, methods and compositions for stimulating angiogenesis, as well as methods and compositions for inhibiting angiogenesis are both desirable. In certain aspects, the invention provides methods and compositions for modulating angiogenesis. In a preferred embodiment, the invention provides methods and compositions for treating angiogenesis associated diseases.

In certain embodiments, the invention provides methods of modulating angiogenesis by administering substantially purified D1-1, or D1-1 agonists or antagonists, or D1-1 binding agents, or D1-1 antisera or antisera directed against D1-1 antisera to a patient. Additional methods include administration of D1-1, D1-1 fragments, D1-1 antisera, or D1-1 receptor agonists and antagonists linked to cytotoxic agents. It is to be understood that the D1-1 can be animal or human in origin.

The present invention further includes methods of modulating angiogenesis by altering (including increasing or decreasing) the production and/or activity of D1-1. Exemplary methods for inhibiting the production of D1-1 include: decreasing D1-1 level by administrating D1-1 inhibitory nucleic acids such as RNAi constructs, antisense oligonucleotides, ribozyme, and DNA enzymes.

Another method of modulating angiogenesis is by blocking the action of excess endogenous D1-1. This can be done by passively immunizing a human or animal with antibodies specific for the undesired D1-1 in the system. This provides a useful tool to examine the effects of D1-1 removal on metastatic processes. The Fab fragment of D1-1 antibodies contains the binding site for D1-1. This fragment is isolated from D1-1 antibodies using techniques known to those skilled in the art. The Fab fragments of D1-1 antisera are used as antigens to generate production of anti-Fab fragment serum. Infusion of this antiserum against the Fab fragments of D1-1 prevents D1-1 from binding to D1-1 antibodies. Therapeutic benefit is obtained by neutralizing endogenous anti-D1-1 antibodies by blocking the binding of D1-1 to the Fab fragments of anti-D1-1. The net effect of this treatment is to facilitate the ability of endogenous circulating D1-1 to reach target cells.

It is to be understood that among the angiogenesis modulating agents of the present invention, those that can stimulate angiogenesis will be useful in treating diseases involving inadequate angiogenesis, whereas those that can inhibit angiogenesis will be useful in treating diseases involving excess angiogenesis.

In a further aspect, the invention includes methods of treating or preventing angiogenesis associated diseases by administrating to a subject in need of substantially purified truncated extracellular D1-1 polypeptides with angiogenesis inhibitory activities. The invention further includes methods of treating or preventing angiogenesis associated diseases by administrating to a subject in need of substantially purified truncated extracellular D1-1 polypeptide fusion proteins with angiogenesis inhibitory activities.

The present invention also encompasses gene therapy whereby the gene encoding D1-1 is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335-356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen.

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of endothelial cell proliferation inhibitor DNA or inhibitor regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

The present invention further provides methods and compositions for targeting therapeutics to cells involved in angiogenesis, thus providing targeted drug delivery when desired. It is contemplated that a drug may be coupled to an antibody directed against an extracellular epitope of the D1-1 protein. The D1-1 antibody can direct the associated drug to only D1-1 expressing cells and achieve targeted drug delivery.

In certain embodiments, the proteins, nucleic acid sequences, antibodies and agents of the present invention are useful for diagnosing and treating angiongenesis associated diseases and processes. Angiogenesis associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, neovascular glaucoma, retrolental fibroplasia, arthritis, diabetic neovascularization, fractures, vasculogenesis, hematopoiesis.

The methods and compositions of the present invention are also useful for modulating physiological processes associated with angiogenesis, for example, ovulation, menstruation, and placentation. The angiogenesis inhibiting proteins of the present invention are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helicobacter pylori*).

The angiogenesis inhibiting proteins of the present invention can be used as a birth control agent by reducing or preventing uterine vascularization required for embryo implantation. Thus, the present invention provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possibly a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that administration of angiogenesis inhibiting agents of the present invention will interfere with normal enhanced vascularization of the placenta, and also with the development of vessels within a successfully implanted blastocyst and developing embryo and fetus.

Conversely, another aspect of the invention provides angiogenesis stimulating agents that promote endothelialization and vascularization. Such effects may be desirable in situations of inadequate vascularization of the uterine endometrium and associated infertility, wound repair, healing of cuts and incisions, treatment of vascular problems in diabetics, especially retinal and peripheral vessels, promotion of vascularization in transplanted tissue including muscle and skin, promotion of vascularization of cardiac muscle especially following transplantation of a heart or heart tissue and after bypass surgery, promotion of vascularization of solid and relatively avascular tumors for enhanced cytotoxin delivery, and enhancement of blood flow to the nervous system, including but not limited to the cerebral cortex and spinal cord.

According to the present invention, D1-1 may be used in combination with other compositions and procedures for the treatment of diseases. For example, a tumor may be treated conventionally with surgery, radiation or chemotherapy combined with D1-1 and then D1-1 may be subsequently administered to the patient to extend the dormancy of micrometastases and to stabilize any residual primary tumor.

Angiogenesis-inhibiting agents can also be given prophylactically to individuals known to be at high risk for developing new or re-current cancers. Accordingly, an aspect of the invention encompasses methods for prophylactic prevention of cancer in a subject, comprising administrating to the subject an effective amount of a truncated extracellular D1-1 polypeptide and/or a derivative thereof, or another angiogenesis-inhibiting agent of the present invention.

9. Formulations and Effective Doses

Pharmaceutical compositions for use in accordance with the present invention may be formulated in conventional manner using one or more physiologically acceptable carriers or excipients. The therapeutic compositions of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the therapeutic compositions of the invention can be formulated in liquid solutions, preferably in physiologically compatible buffers such as Hank's solution or Ringer's solution. In addition, the therapeutic compositions may be formulated in solid form and redissolved or suspended immediately prior to use. Lyophilized forms are also included.

For oral administration, the therapeutic compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active agent. For buccal administration the therapeutic compositions may take the form of tablets or lozenges formulated in conventional manner. For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the therapeutic agents and a suitable powder base such as lactose or starch.

The therapeutic compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition to the formulations described previously, the therapeutic compositions may also be formulated as a depot preparation. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention are formulated into ointments, salves, gels, or creams as generally known in the art. A wash solution can be used locally to treat an injury or inflammation to accelerate healing. For oral administration, the therapeutic compositions are formulated into conventional oral administration forms such as capsules, tablets, and tonics.

The therapeutic compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the nucleic acids of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection, the nucleic acids of the invention can be formulated in liquid solutions, preferably in physiologically compatible buffers such as Hank's solution or Ringer's solution. In addition, the nucleic acids may be formulated in solid form and redissolved or suspended immediately prior to use. Lyophilized forms are also included.

Toxicity and therapeutic efficacy of therapeutic compositions of the present invention can be determined by standard pharmaceutical procedures in cell cultures or experimental animals, e.g., for determining The Ld50 (The Dose Lethal To 50% Of The Population) And The Ed50 (the dose therapeutically effective in 50% of the population). The dose ratio between toxic and therapeutic effects is the therapeutic index and it can be expressed as the ratio LD50/ED50. Therapeutic agents which exhibit large therapeutic induces are preferred. While therapeutic compositions that exhibit toxic side effects may be used, care should be taken to design a delivery system that targets such therapeutic agents to the site of affected tissue in order to minimize potential damage to uninfected cells and, thereby, reduce side effects.

The data obtained from the cell culture assays and animal studies can be used in formulating a range of dosage for use in humans. The dosage lies preferably within a range of circulating concentrations that include the ED50 with little or no toxicity. The dosage may vary within this range depending upon the dosage form employed and the route of administration utilized. For any agents used in the method of the invention, the therapeutically effective dose can be estimated initially from cell culture assays. A dose may be formulated in animal models to achieve a circulating plasma concentration range that includes the IC50 (i.e., the concentration of the test therapeutic agent which achieves a half-maximal inhibition of symptoms) as determined in cell culture. Such information can be used to more accurately determine useful doses in humans. Levels in plasma may be measured, for example, by high performance liquid chromatography.

The practice of aspects of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Identification of Novel Angiogenesis-Related Nucleic Acids

D1-1 was identified in a differential screen of a cDNA library generated from an individual arterial endothelial cell from E10.5 mouse embryos. A single clone for D1-1 was isolated from this screen, and contained primarily 3' untranslated sequences. Subsequently, the sequence of the D1-1 cDNA clone was used to search mouse genomic and EST sequence databases, in order to identify related and overlapping sequences. These sequences were assembled into an overlapping series of contiguous clones. This "contig" was used to reconstruct a single sequence shown below. This sequence predicted a long open reading frame (ORF) bounded at the 5' end by an initiator codon (ATG) and a termination codon (TAA). This sequence is accurate to within the limits of accuracy of the sequences we extracted from the electronic database.

Figure 1:
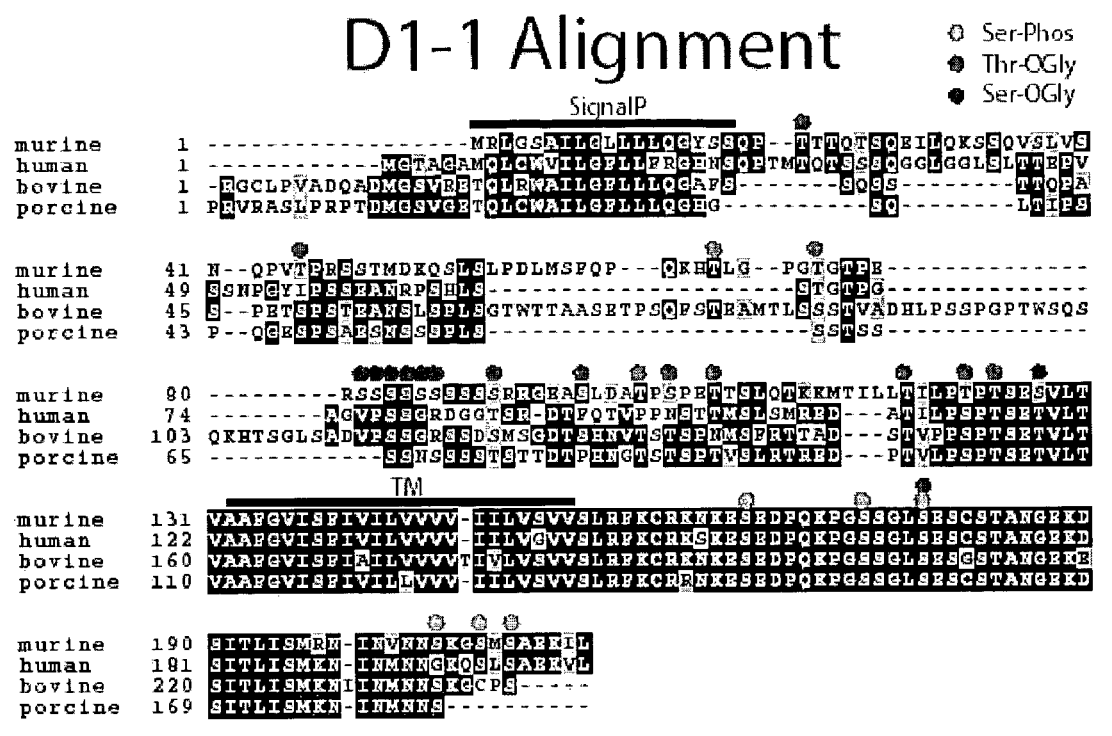

The predicted amino acid sequence from the ORF was analyzed by a program that identifies stretches of hydrophobic amino acids. This program predicted a hydrophobic sequence at the amino terminus (18 aa), and a second stretch of 23 hydrophobic amino acids beginning at residue 132 (FIG. 1). These data suggest that the N-terminal hydrophobic sequence is a signal peptide, and the second, longer stretch a transmembrane segment. The transmembrane segment is strongly evolutionarily conserved, as is the sequence immediately C-terminal to it, which is predicted to be cytoplasmic. The cytoplasmic domain is predicted to contain numerous consensus Serine phosphorylation sites, suggesting it is involved in signal transduction like other Type I transmembrane receptors. The sequence between the N-terminal signal peptide and the putative transmembrane segment is predicted to be extracellular. Consistent with this, the sequence has numerous consensus sites for O-glycosylation. It is also less evolutionarily conserved than the transmembrane and cytoplasmic domains, as is characteristic of the extracellular domains of other transmembrane proteins. Together, these data predict that D1-1 is a "Type 1" transmembrane protein: a protein with a single membrane-spanning segment whose N-terminus is extracellular and whose C-terminus is cytoplasmic (intracellular).

D1-1 amino acid and encoding nucleic acid sequences from various species were further identified. D1-1 amino acid and nucleic acid sequences are shown in FIGS. 5-12. Additional examples of a murine D1-1 amino acid and nucleic acid sequences may be found in Genbank ref. nos. XM_148854 and XP_148854. Additional examples of human D1-1 amino acid and nucleic acid sequences may be found in the following patent publications: EP 0 682 113 A2; WO 00/55173; WO 00/61623; WO 01/57190; WO 01/77289; WO 02/059271; WO 02/079492.

Alignments of D1-1 amino acids (FIG. 1) and nucleic acids demonstrate the existence of a family of D1-1 polypeptides and nucleic acids containing a C-terminal domain that is highly conserved across different species. Pairwise full-length and domain comparisons between family members are shown in Tables 1-3. Alignments were performed using the pairwise BLAST algorithm available through NCBI.

TABLE 1

Pairwise comparison of full-length D1-1 amino acid sequences (percent identity)

| D1-1 Sources: | Human | Bovine | Murine | Porcine |
|---|---|---|---|---|
| Human | 100% | — | — | — |
| Bovine | 54% | 100% | — | — |
| Murine | 56% | 54% | 100% | — |
| Porcine | 61% | 57% | 55% | 100% |

TABLE 2

Pairwise comparison of conserved region of D1-1 amino acid sequences (percent identity)

| D1-1 Sources: | Human | Bovine | Murine | Porcine |
|---|---|---|---|---|
| Human | 100% | — | — | — |
| Bovine | 88% | 100% | — | — |
| Murine | 90% | 87% | 100% | — |
| Porcine | 94% | 89% | 94% | 100% |

TABLE 3

Pairwise comparison of extracellular portion of D1-1 amino acid sequences (percent identity)

| D1-1 Sources: | Human | Bovine | Murine | Porcine |
|---|---|---|---|---|
| Human | 100% | — | — | — |
| Bovine | 38% | 100% | — | — |
| Murine | 33% | 37% | 100% | — |
| Porcine | 47% | 54% | 35% | 100% |

EXAMPLE 2

Expression of D1-1 in Developing Mouse Embryos

Figure 3:
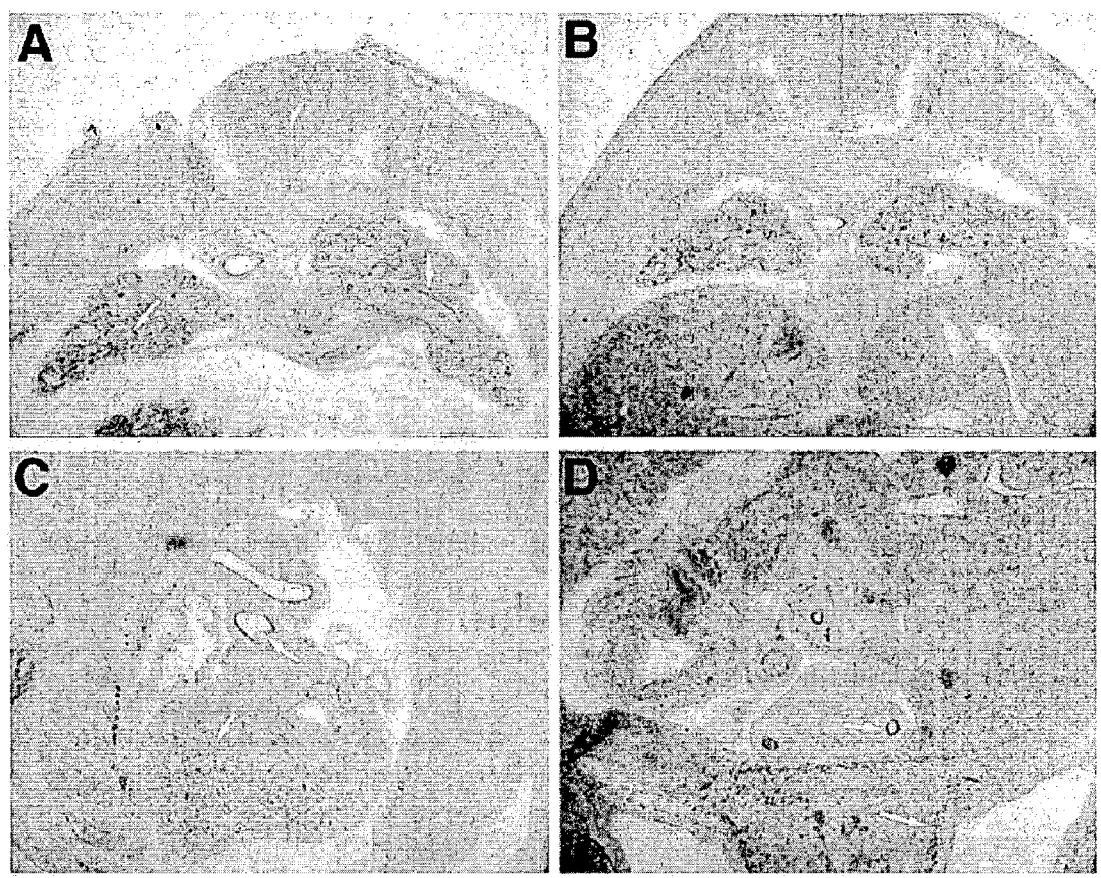
FIG. 3. In situ hybridization of day 13.5 (E13.5) mouse embryos with a D1-1 cRNA probe. White arrows indicate the specific expression of D1-1 in the endothelium and endocardium of the heart (C). Specific expression is not detected in any other tissues at this stage.

Expression of D1-1 in developing mouse embryos was examined by in situ hybridization of day 10.5 (E10.5) and day 13.5 (E13.5) mouse embryos using a D1-1 cRNA probe. FIG. 2 shows that D1-1 is specifically expressed in endothelium (arrow). No D1-1 expression is detected in any other tissues at this stage. FIG. 3 shows the specific expression of D1-1 in the endothelium and endocardium of the heart (C). Specific expression is not detected in any other tissues at this stage.

Figure 13:
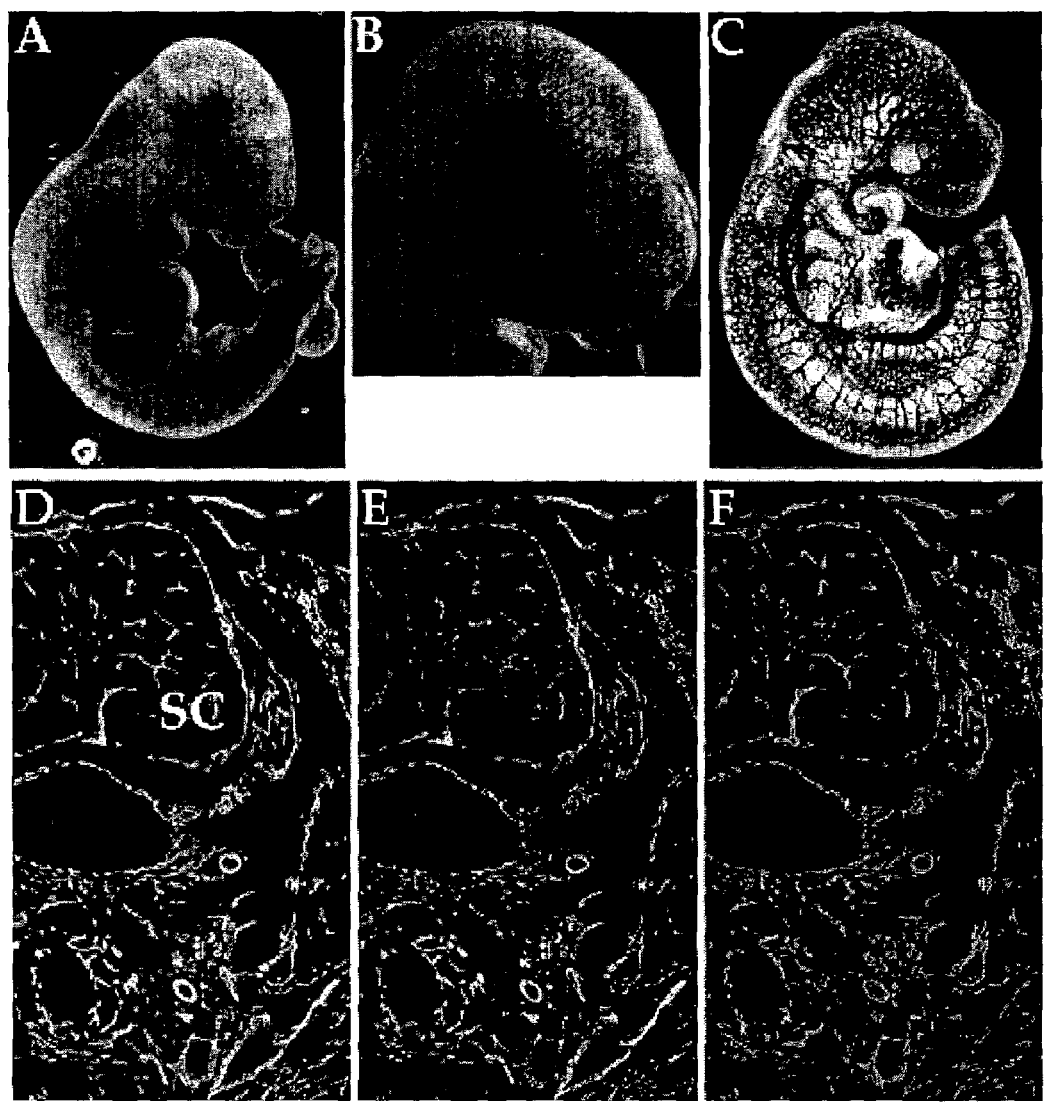
FIG. 13: tau-lacZ knock-in homozygous E10.5 mouse embryo, designed so as to express the lacZ marker gene in a manner consistent with D1-1 expression: whole mount X-gal staining (A) and high magnification of the head region (B). E9.5 wild type embryo whole mount PECAM staining (C). tau-lacZ knock-in heterozygous embryo section staining of the neck region (D) and green is beta-galactosidase antibody staining (E) and red is PECAM antibody staining (F). In (D), SC denotes spinal cord.
Figure 14:
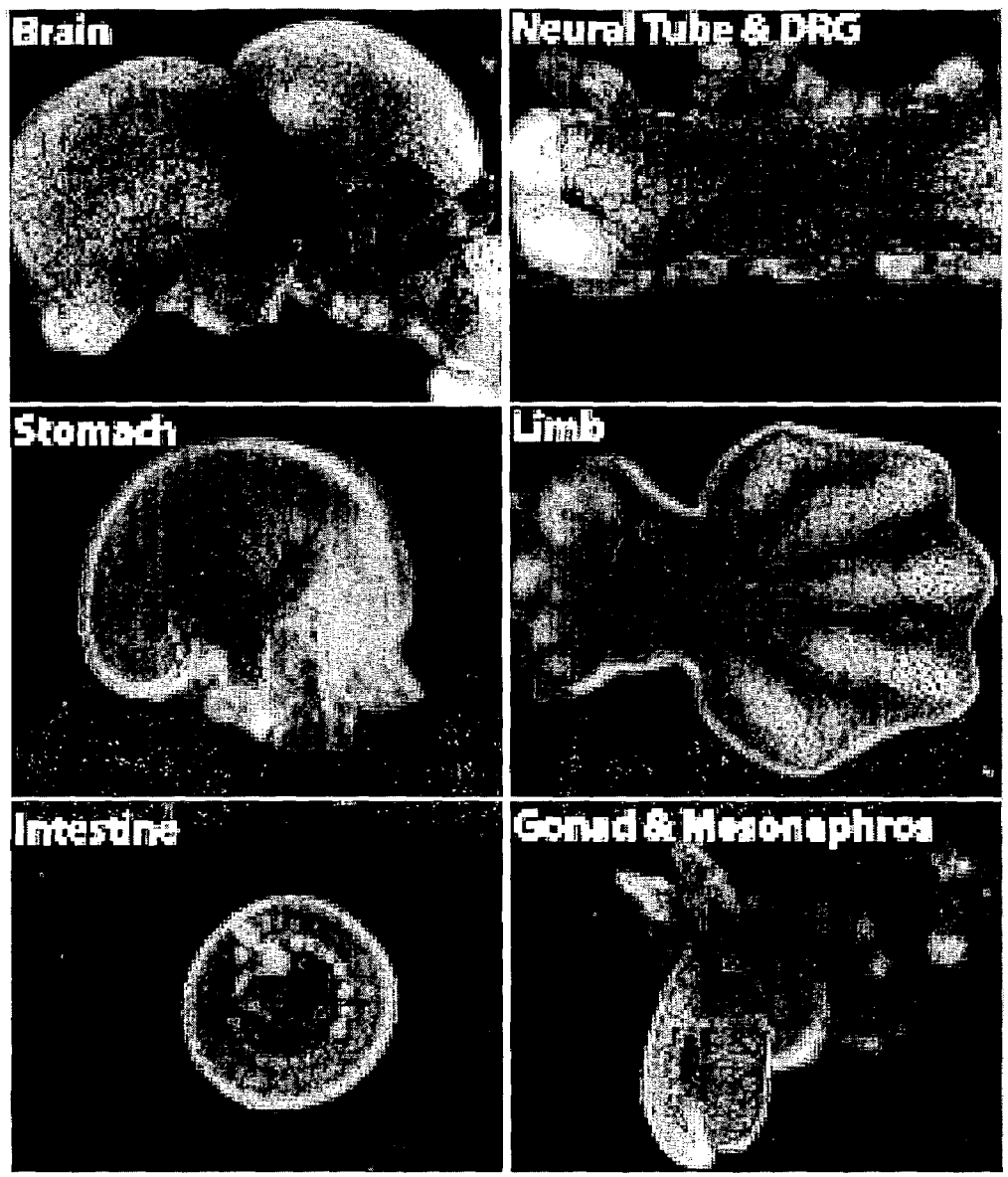
FIG. 14: tau-lacZ knock-in homozygous E13.5 mouse embryo: organ whole mount X-gal staining.

Expression in the endothelium of embryonic and adult mice was confirmed by generating knock-in mice carrying a tau-LacZ fusion to visualize the expression patterns of D1-1. D1-1 expression patterns were measured at E10.5 in an embryo and in adult females by X-gal staining. D1-1 is specifically expressed in endothelial cells of both embryos and an adult (FIGS. 13 and 14). D1-1 expression corresponds closely with expression of PECAM, a specific marker for endothelial cells.

EXAMPLE 3

Subcellular Distribution of D1-1 Protein

Figure 4:
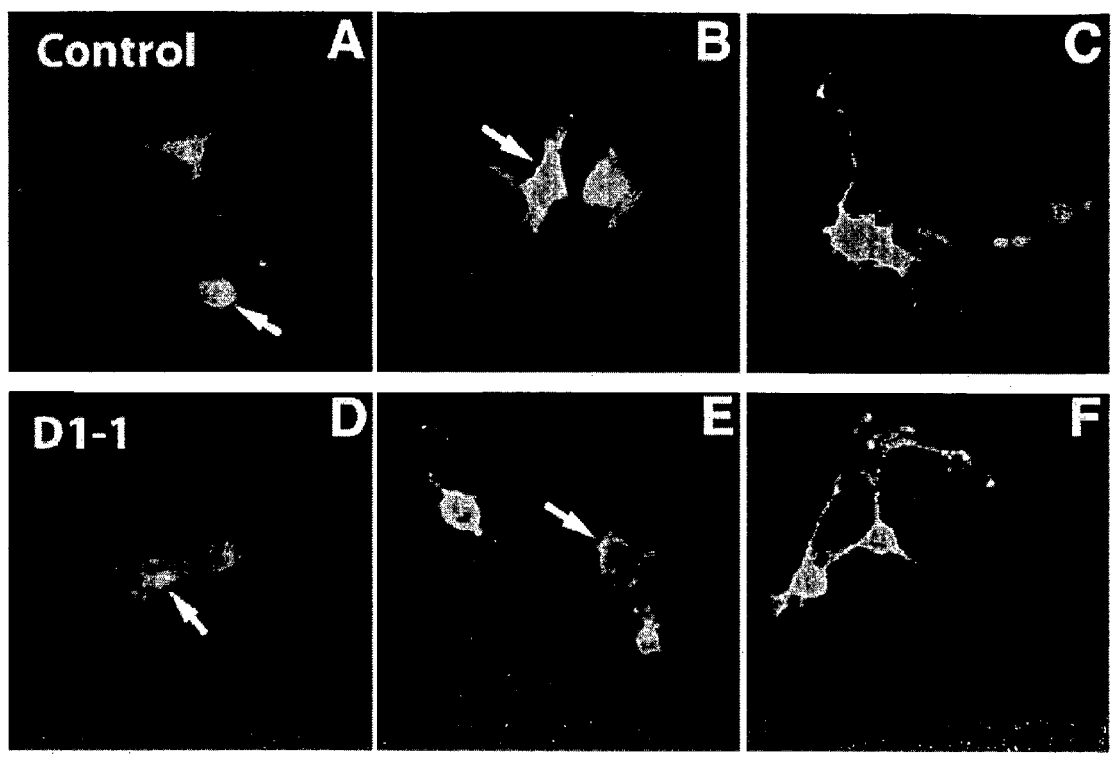
FIG. 4. Subcellular distribution of a D1-1::GFP fusion protein expressed in COS 7 cells. The cells were stained with an anti-GFP antibody and developed using indirect immunofluorescence. Note the perinuclear staining of D1-1::GFP (D, arrow), that is characteristic of membrane proteins and distinct from the uniform cytoplasmic staining shown by GFP alone (A, arrow). Surface membrane-associated expression of D1-1::GFP is visible in E (arrow).

To confirm the predicted membrane localization of D1-1, the coding sequence was fused at its C-terminus to sequences encoding either the Green Fluorescent Protein (GFP) or a short "epitope tag" called V5. These two modified forms of D1-1 were then expressed in cultured mammalian COS-7 cells by cloning them into a eukaryotic expression plasmid and transfecting the plasmid into the cells. After 24-48 hrs, the cells were fixed and the subcellular distribution of the D1-1 fusion proteins analyzed by indirect immunofluorescence, using either antibodies to GFP (FIG. 4) or to the V5 epitope tag. These experiments revealed a subcellular distribution of the D1-1-GFP fusion that is characteristic of membrane proteins, and clearly distinct from the distribution of cytoplasmic proteins as evidenced by comparison to the staining pattern of cells expressing GFP alone (FIG. 5, arrows).

This membrane localization of D1-1 was confirmed using the V5-epitope tagged form (not illustrated).

EXAMPLE 4

A Truncated Extracellular D1-1 Fragment Inhibits Angiogenesis

To study the function of D1-1 protein, we constructed a truncated extracellular D1-1::Fc fusion protein. The D1-1::Fc fusion protein contains the N-terminal 130 amino acids of the murine D1-1 protein, followed by a GTGPG linker, fused with a human Fc fragment. The sequences of the D1-1::Fc fusion protein are shown below. The D1-1::Fc fusion protein was purified using baculovirus system.

Figure 15:
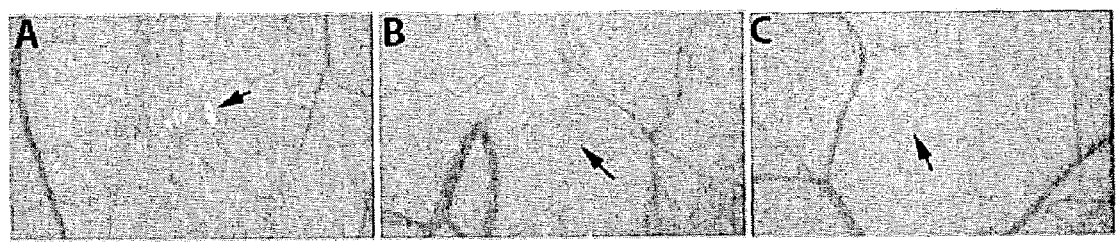
FIG. 15: Chorioallantoic membrane (CAM) assay of D1-1: Fc Fusion Proteins. Panels A, B, and C show increasing inhibition of blood vessel development in response to increasing amounts of D1-1:Fc fusion protein. 0 μg (A), 2 μg (B), and 4 μg (C) of D1-1 Fc proteins were used to make the methylcellulose pellets and were applied to a CAM assay. The arrows denote the position of the methylcellulose pellets containing D1-1 Fc proteins.

The purified D1-1::Fc fusion protein was then used to perform a chick chorioallantoic membrane (CAM) assay. The results from the CAM assay demonstrated that D1-1::Fc fusion protein has strong angiogenesis inhibitor activity (FIG. 15). The D1-1:Fc fusion protein was further tested and showed similar activity when used in a rigorously controlled CAM assay employing an Fc fragment prepared from an identical cell line as a control.

Nucleotide and amino acid sequence of a mouse-derived truncated extracellular D1-1 polypeptide (a D1-1::Fc fusion protein) used in the CAM assay (1104 nucleotides, the first portion is derived from mouse D1-1, followed by the linker coding sequences in all capital letters and then the Fc portion).

```
1104nt                                                    (SEQ ID NO:25)
atgaggctgggttcagcaattctcggtttactcctgctccaaggctacagctctcaacctacgacaac tcagacctcgcaggaaattctacagaagtcttctcaggtctccttggtatccaatcagcctgtgacac caaggtcaagcaccatggataaacagtcccttctccttgcctgacttgatgtcttccagccacagaag cacacactgggacctggcacaggaacccagaaaggagcagcagcagcagcagcagcagcagcagcag
```

```
gagaggagaagcatctctggatgctactcccagtccagaaaccaccagccttcagacaaaaaagatga
ccatcctgctgaccatcctgcctaccccacatcagagtcagtgctaact
```

GGTACC GGA CCA GGA

```
gagcccaaatcttgtgacaaaactcacacatgcccaccgtgcccagcacctgaactcctggggggacc
gtcagtcttcctcttccccccaaaacccaaggacaccctcatgatctcccggaccctgaggtcacat
gcgtggtggtggacgtgagccacgaagaccctgaggtcaagttcaactggtacgtggacggcgtggag
gtgcataatgccaagacaaagccgcgggaggagcagtacaacagcacgtaccgtgtggtcagcgtcct
caccgtcctgcaccaggactggctgaatggcaaggagtacaagtgcaaggtctccaacaaagccctcc
cagcccccatcgagaaaaccatctccaaagccaaagggcagccccgagaaccacaggtgtacaccctg
cccccatcccgggaggagatgaccaagaaccaggtcagcctgacctgcctggtcaaaggcttctatcc
cagcgacatcgccgtggagtgggagagcaatgggcagccggagaacaactacaagaccacgcctcccg
tgctggactccgacggctccttcttcctctacagcaagctcaccgtggacaagagcaggtggcagcag
gggaacgtcttctcatgctccgtgatgcatgaggctctgcacaaccactacacgcagaagagcctctc
cctgtctccgggtaaa
```
tga

Protein sequence of mouse D1-1::Fc fusion protein (shown with signal sequence), with the linker sequence underlined (367 amino acids)

(SEQ ID NO:26)
MRLGSAILGLLLLQGYSSQPTTTQTSQEILQKSSQVSLVSNQPVTPRSST
MDKQSLSLPDLMSFQPQKHTLGPGTGTPERSSSSSSSSSSRRGEASLDAT
PSPETTSLQTKKMTILLTILPTPTSESVLT<u>GTGPG</u>EPKSCDKTHTCPPCP
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHE
ALHNHYTQKSLSLSPGK

An example of a nucleic acid sequence that would encode a human-derived D1-1:Fc fusion protein:

(SEQ ID NO:27)
GAGCCTCCACTGAGCTGCTGCCTGCCCGCCACATACCCAGCTGACATGGGCACCGCAGGA
GCCATGCAGCTGTGCTGGGTGATCCTGGGCTTCCTCCTGTTCCGAGGCCACAACTCCCAG
CCCACAATGACCCAGACCTCTAGCTCTCAGGGAGGCCTTGGCGGTCTAAGTCTGACCACA
GAGCCAGTTTCTTCCAACCCAGGATACATCCCTTCCTCAGAGGCTAACAGGCCAAGCCAT
CTGTCCAGCACTGGTACCCCAGGCGCAGGTGTCCCCAGCAGTGGAAGAGACGGAGGCACA
AGCAGAGACACATTTCAAACTGTTCCCCCCAATTCAACCACCATGAGCCTGAGCATGAGG
GAAGATGCGACCATCCTGCCCAGCCCCACGTCAGAGACTGTGCTCACT

GGTACC GGA CCA GGA

```
gagcccaaatcttgtgacaaaactcacacatgcccaccgtgcccagcacctgaactcctggggggacc
gtcagtcttcctcttccccccaaaacccaaggacaccctcatgatctcccggaccctgaggtcacat
gcgtggtggtggacgtgagccacgaagaccctgaggtcaagttcaactggtacgtggacggcgtggag
gtgcataatgccaagacaaagccgcgggaggagcagtacaacagcacgtaccgtgtggtcagcgtcct
caccgtcctgcaccaggactggctgaatggcaaggagtacaagtgcaaggtctccaacaaagccctcc
cagcccccatcgagaaaaccatctccaaagccaaagggcagccccgagaaccacaggtgtacaccctg
cccccatcccgggaggagatgaccaagaaccaggtcagcctgacctgcctggtcaaaggcttctatcc
cagcgacatcgccgtggagtgggagagcaatgggcagccggagaacaactacaagaccacgcctcccg
```

```
tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatga
```

An example of a human-derived D1-1:Fc fusion protein (with signal sequence):

(SEQ ID NO:28)
QPTMTQTSSSQGGLGGLSLTTEPVSSNPGYIPSSEANRPSHLSSTGTPGA

GVPSSGRDGGTSRDTFQTVPPNSTTMSLSMREDATILPSPTSETVLT<u>GTG</u>

<u>PG</u>EPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTVD

KSRWQQGNVFSCSVMHEALHNHYTQKSLSLSPGK

EXAMPLE 5

Assays for Modulators of Angiogenesis

Modulators of angiogenesis can be identified by screening for agents that alter (decrease or increase) the angiogenesis inhibitor activity of the D1-1::Fc fusion protein in following assays.

Chick Chorioallantoic Membrane (CAM) Assay

The early chick embryo lacks a mature immune system and therefore can be used to study tumor-induced angiogenesis. In this assay, tissue grafts are placed on the CAM through a window made in the eggshell. This causes a typical radial rearrangement of vessels towards, and a clear increase of vessels around the graft within four days after implantation. Blood vessels entering the graft are counted under a stereomicroscope. To assess the anti-angiogenic or angiogenic activity of test substances, the therapeutic agents are generally prepared in slow release polymer pellets, absorbed by gelatin sponges or air-dried on plastic discs and then implanted onto the CAM. Several variants of the CAM assay including culturing of shell-less embryos in Petri dishes, and different quantification methods (i.e. measuring the rate of basement membrane biosynthesis using radio-labeled proline, counting the number of vessels under a microscope or image analysis) have been described. The CAM assay is relatively simple and inexpensive and thus suitable for large-scale screening.

As described above, a truncated extracellular D1-1 polypeptide that is a D1-1:Fc fusion protein has been demonstrated to have an antiangiogenic effect in the CAM assay. Modulators of angiogenesis can be identified by screening for agents that alter (decrease or increase) the angiogenesis inhibitor activity of the D1-1::Fc fusion protein in CAM assays.

Corneal Pocket Assay

The cornea presents an in vivo avascular site. Therefore, any vessels penetrating from the limbus into the corneal stroma can be identified as newly formed. To induce an angiogenic response, slow release polymer pellets [i.e. poly-2-hydroxyethyl-methacrylate (hydron) or ethylene-vinyl acetate copolymer (ELVAX)] containing an angiogenic substance (i.e. FGF-2 of VEGF) are implanted in "pockets" created in the corneal stroma of a rabbit. Also, a wide variety of tissues, cells, cell extracts and conditioned media have been examined for their effect on angiogenesis in the cornea. The vascular response can be quantified by computer image analysis after perfusion of the cornea with India ink. Corneal assays can also be performed using the cornea of a mouse.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method for inhibiting angiogenesis in a mammal, comprising administering to the mammal in need thereof an angiogenesis inhibiting amount of a polypeptide comprising an extracellular portion of a D1-1 polypeptide having:
   a) an amino acid sequence that is at least 95% identical to SEQ ID NO: 11; or,
   b) an amino acid sequence encoded by a nucleic acid sequence that is at least 99% identical to SEQ ID NO: 8
   wherein the polypeptide has angiogenesis inhibitory activity.

2. The method of claim 1, wherein the extracellular portion of the D1-1 polypeptide is SEQ ID NO: 11.

3. The method of claim 1, wherein the method further comprises administering another agent that modulates angiogenesis.

4. The method of claim 1, wherein the amino acid sequence of the extracellular portion of the D1-1 polypeptide is at least 98% identical to SEQ ID NO: 11.

5. The method of claim 4, wherein the method further comprises administering another agent that modulates angiogenesis.

6. The method of claim 2, wherein the method further comprises administering another agent that modulates angiogenesis.

* * * * *